(12) United States Patent
Kunaparaju et al.

(10) Patent No.: US 7,919,270 B2
(45) Date of Patent: Apr. 5, 2011

(54) MAMMALIAN EXPRESSION SYSTEM

(75) Inventors: Rajkumar Kunaparaju, Waterloo (AU);
Noelle-Ann Sunstrom, La Perouse (AU)

(73) Assignee: Acyte Biotech Pty Ltd, Sydney (AU)

( * ) Notice: Subject to any disclaimer, the term of this patent is extended or adjusted under 35 U.S.C. 154(b) by 1046 days.

(21) Appl. No.: 10/938,864

(22) Filed: Sep. 9, 2004

(65) Prior Publication Data
US 2005/0227317 A1 Oct. 13, 2005

Related U.S. Application Data

(60) Provisional application No. 60/501,655, filed on Sep. 9, 2003.

(51) Int. Cl.
*C12P 21/02* (2006.01)

(52) U.S. Cl. .................. 435/69.1; 435/358; 435/320.1

(58) Field of Classification Search .................. None
See application file for complete search history.

(56) References Cited

U.S. PATENT DOCUMENTS 5,374,515 A * 12/1994 Parenteau et al. ............ 435/1.1
5,798,105 A * 8/1998 Schoenmakers et al. .. 424/272.1

OTHER PUBLICATIONS

DeWaele et al., Eur. J. Biochem. vol. 176, pp. 287-295 (1988).*
Heinzel et al., "Use of Simian Virus 40 Replication to Amplify Epstein-Barr Virus Shuttle Vectors in Human Cells", Journal of Virology, 1988, 62(10), pp. 3738-3746.
Stary and Sarasin,"Simian virus 40 (SV40) large T antigen-dependent amplification of an Epstein-Barr virus-SV40 hybrid shuttle vector integrated into the human HeLa cell genome", Journal of General Virology, 1992, 73, pp. 1679-1685.
Haase et al., "Improved EBV shuttle vectors", Mutation Research, 1989, 220, pp. 125-132.
Piechaczek et al.,"A vector based on the SV40 origin of replication and chromosomal S/MARs replicates episomally in CHO cells", Nucleic Acids Research, 1999, 27(2), pp. 426-428.
International Search Report of PCT/AU2004/001224, (2005).
Mizuguchi H et al, "Long-term replication of Epstein-Barr virus-derived episomal vectors in the rodent cells", Febs Letters, Elsevier, Amsterdam, NL, vol. 472, No. 2-3, Apr. 28, 2000, pp. 173-178.
Heffernan M et al, "Polyoma and Hamster papovavirus large T antigen-mediated replication of expression shuttle vectorsin Chinese hamster ovary cells" Nucleic Acids Research, Oxford University Press, Surry, GB, vol. 19, No. 1, 1991, pp. 85-92.
Andersen Dana C et al, "Recombinant protein expression for therapeutic applications", Current Opinion in Biotechnology, vol. 13, No. 2, Apr. 2002, pp. 117-123.
Kunaparaju Rajkumar et al, Epi-CHO, an episomal expression system for recombinant protein production in CHO cells, Biotechnology and Bioengineering, vol. 91, No. 6, Sep. 2005, pp. 670-677.
Pham P L et al, "Large-scale transient transfection of serum-free suspension-growing HEK293 EBNA1 cells: Peptone additives improve cell growth and transfection efficiency", Biotechnology and Bioengineering, Wiley & Sons, Hoboken, NJ, US, vol. 84, No. 3, Nov. 5, 2003, pp. 332-342.
Meissner P et al, "Transient gene expression: Recombinant protein production with suspension-adapted HEK293-EBNA cells", Biotechnology and Bioengineering—Combinatorial Chemistry Wiley, New York, US, vol. 75, No. 2, Oct. 20, 2001, pp. 197-203.
Polvino-Bodnar M et al, "DNA binding activity is required for EBNA 1-dependent transcriptional activation and DNA replication", Virology, vol. 187, No. 2, 1992, pp. 591-603.
European Search Report re: EP 04 81 6094, dated Jun. 8, 2007.

* cited by examiner

*Primary Examiner* — James S Ketter
(74) *Attorney, Agent, or Firm* — Edwards Angell Palmer & Dodge LLP; Jeffrey D. Hsi; Elizabeth Spar

(57) ABSTRACT

The present invention relates to protein expression systems and in particular to a mammalian protein expression system. Specifically, the present invention provides a rodent cell line with enhanced protein production capabilities.
The invention also relates to eukaryotic cloning and expression vectors and related methods, and in particular to DNA vectors capable of high level expression of a protein of interest. The invention allows for long-term episomal maintenance of expression vectors in mammalian cells.

18 Claims, 22 Drawing Sheets

MAMMALIAN EXPRESSION SYSTEM

CROSS REFERENCE TO RELATED APPLICATIONS

This application claims priority under 35 U.S.C. §119(e)(1) of U.S. Provisional Application Ser. No. 60/501,655, filed Sep. 9, 2003, and claims benefit under 35 USC §119, of Australia provisional application serial number 2004901233, filed Mar. 10, 2004. The disclosure of the prior applications are considered part of and incorporated by reference in the disclosure of this application.

TECHNICAL FIELD

The present invention relates to protein expression systems and in particular to a mammalian protein expression system. Specifically, the present invention provides a rodent cell line with enhanced protein production capabilities.

The invention also relates to eukaryotic cloning and expression vectors and related methods, and in particular to DNA vectors capable of high level expression of a protein of interest. The invention allows for long-term episomal maintenance of expression vectors in mammalian cells.

BACKGROUND

Any discussion of the prior art throughout the specification should in no way be considered as an admission that such prior art is widely known or forms part of common general knowledge in the field.

In recombinant protein production, the choice of host cell is very important. Many expression systems for recombinant proteins are available and include bacteria, yeast, fungi, insect, plant and mammalian cells. The suitability of each host cell for recombinant protein expression differs significantly and affects both the product formation and subsequent isolation/purification of the final protein produced. Expression systems such as bacteria are incapable of producing specific classes of proteins, which require post-translational modifications such as glycosylation for bioactivity. Furthermore, many therapeutic proteins require complex post-translational modifications such as glycosylation in order to be biologically active.

The use of mammalian expression systems for producing therapeutic recombinant proteins has been well documented. Mammalian cells have the ability to carry out authentic protein folding and complex post-translational modifications, which are necessary for the therapeutic activity of many proteins. As such, many host cell lines have been approved by regulatory bodies for use in the production of therapeutic proteins.

Expression systems such as human cell lines 293 and PER.C6, have been proposed as hosts for the production of recombinant human therapeutic proteins. These cell lines were developed by transforming human embryonic kidney cells (293) and human embryonic retinal cells (PER.C6) with the transforming early region (E1) of adenovirus type 5 (ad5). Since cell lines such as 293 and PER.C6 express the Ad5 E1 region, they are able to complement the growth of defective Ad5 vectors, which have been crippled by deletion of E1. However, a feature of regulatory importance associated with Ad5-transformed cells is their capacity to form tumours in immunodeficient animals such as nude mice. Therefore, the use of Ad5-transformed cells poses a potential oncogenic risk i.e. the risk of transmitting the tumorigenic components of the cell substrate used for recombinant protein to the subject being treated.

Chinese hamster ovary cell lines are routinely used for the production of biopharmaceutical proteins. A number of characteristics make CHO cells very suitable as host cells: high product levels can be reached in CHO cells; they provide a safe production system free of infectious or virus-like particles; they have been characterized extensively; they can grow in suspension to high cell densities in bioreactors, using serum-free culture media; expression systems for gene amplification in CHO cells have been described (DHFR, GS and metallothionein (MT); Page and Sydenham, 1991, Baker et al, 2001 and Bailey et al 2002).

The cell line CHO-K1 has formed the basis for the generation of a variety of CHO cell line derivatives with improved characteristics, such as the Super-CHO cell line (Pak et al 1996). Super-CHO cells were derived from CHO-K1 cells which were genetically engineered to express the genes encoding transferrin and the growth factor, IGF-1.

Polyoma Virus

Polyomaviruses are a family of small DNA tumour viruses comprising the simian virus 40 (SV40) and the mouse polyoma virus.

Polyomaviruses have served as models to study mammalian gene expression, DNA replication and tumorigenesis (Griffin, 1982). The COS-1 cell line supports episomal replication of SV40 origin containing plasmids (Gluzman, 1981) and was developed by transforming CV1 cells with an origin defective mutant of SV40 virus which codes for wild type T antigen. (Gluzman, 1981). Viruses are host specific and can propagate in their permissive host cells. SV40 virus can propagate in monkey cells (CV1). Py is a mouse virus and can propagate in mice and some rodents.

The large T antigen of Polyomavirus is a multifunctional protein having enzymatic activities and the ability to interact with cellular proteins. It can bind DNA and has two nuclear localization signals. It interacts specifically with several pentameric sequences (GAGGC) at the viral origin of DNA replication. The large T antigen also possesses DNA helicase activity. Helicase activity is crucial for viral DNA replication and requires functional ATPase activity and the ability to bind Polyomavirus DNA.

Replication of Polyomavirus DNA within infected cells requires a specific functional viral origin of DNA replication, large T antigen and a set of cellular proteins known as permissive host factors i.e. the only viral protein necessary for DNA replication is the Large T antigen. Viral DNA replication differs from cellular DNA replication in that the viral origin can fire multiple times during S phase, whereas cellular DNA replication is tightly controlled to prevent any region of the genome from being replicated more than once in a single cell cycle.

A study by Heffernan and Dennis in 1991 (Heffernan and Dennis, 1991) successfully demonstrated the use of eukaryotic expression vectors in viral large T antigen-expressing CHO cells. However, transient expression of the desired protein was shown to only last 48-72 hours. The plasmid was not stably maintained within the cell and was quickly degraded or lost when the cell underwent division.

Episomal replication and stable maintenance of the DNA in mouse embryonic stem cells was also examined by Gassmann et al (Gassmann et al 1995), and in U.S. Pat. No. 2002/0146689, which describes the use of Polyomavirus-based plasmids and the dependence of extrachromosomal replication on the expression of large T antigen.

We have observed that Py based expression vectors (plasmids containing Py origin of DNA replication) like SV40 based vectors can replicate several times within the cell and attain high copy number. In contrast to the COS cell expression system where plasmid replication overwhelms and eventually kills the host cell within a few days of transfection, CHO-T cells transfected with Py-origin containing plasmids do not replicate to such an extent. This is presumably due to the semi-permissive nature of the CHO cell for Py DNA replication. In this system plasmid DNA harbouring the Py ori is lost within 3 days of transfection due to degradation and/or cell division and recombinant gene expression is lost. This limits the time to maximize transient protein production to up to 3 days.

Episomal Vectors

In theory, gene therapy is the delivery of corrective genetic material into cells to alleviate the symptoms of a disease or to correct a defective gene. Optimal vectors for gene therapy require 1) high-level and stable expression of the gene of interest, 2) a high transfection efficiency, 3) no integration into chromosomal DNA to avoid effects on the cell's own DNA, and 4) no transformation features that may result in secondary cancers. Vectors meeting all these criteria are not available. Gene transfer by nonviral vector-mediated systems has been shown to be a safe and simple, but relatively inefficient, method for gene delivery. Many of the systems currently available utilize viral vectors derived from retroviruses and adenoviruses. The use of nonintegrating viruses for the construction of an efficient gene-delivery vector has been intensely studied. In particular, EBV-based expression vectors have been considered.

Epstein-Barr Virus

One method of achieving high expression levels without affecting the cellular genome is to use episomal plasmid vectors which replicate extrachromosomally. Episomal vectors, which replicate extrachromosomally in cells over a long period are useful tools for studying the expression of cloned genes and gene therapy, for example, an Epstein-Barr virus (EBV)-derived plasmid.

Epstein-Barr virus (EBV) is a human gamma herpes virus. The viral elements required for both episomal replication and nuclear retention are the cis-acting replication origin (oriP) of the EBV gene and the EBV nuclear antigen-1 (EBNA-1), which interacts with the oriP region. Plasmids containing the oriP and EBNA-1 sequences are maintained as low-copy number DNA episomes in the cell nucleus and replicate once per cell cycle in primate cells. The chromosome-binding activity of EBNA1 secures the separation to the daughter cells during mitosis.

EBV-based vectors are mainly used in primate cells. The failure of EBV-derived vectors to replicate in most rodent cells, including mouse and hamster, forms a serious drawback for gene therapy, since testing EBV vectors in animals, such as mice, and in culture, such as CHO cells, was previously considered to be impossible. In particular, CHO cells do not support EBV viral DNA replication.

Previous studies using EBV-derived vectors in rodent cells have shown that only some rodent cells (C6 and L6) are capable of replicating plasmids containing EBV oriP and encoding EBNA-1 (Mizuguchi, H. Hosono, T., Hayakawa (2000)), and only for a limited amount of time (i.e <5 days). Replication in CHO cells was only possible when large fragments (21 Kb) of undefined human DNA sequences were inserted in the expression vector (Krysan P. J. and Michele Calos. (1993)). Such large plasmid constructs are not amenable to gene transfer studies due to the unstable and undefined nature of such an expression vector, which affects the production of the potentially therapeutic product. Accordingly, there is a need for an expression plasmid, capable of stable episomal replication and maintenance, without containing large fragments of random human DNA.

Episomal vectors have been used to increase the frequency of stable transfection and to achieve reliable transgene expression in many cell types. However, previously described episomal vectors, for example, based on Epstein Barr Virus (EBV) or SV40 large T antigen have demonstrated limitations both in host cell range and maintenance during long term culture (Piechaczek et al (1999); and Heffernan and Dennis (1991)).

Recently, large-scale transient protein production methods have been described for the rapid production of large amounts of recombinant proteins with yields up to 20 mg/L (Durocher et al 2002; Girard et al 2002; Meissner et al 2001; Jordan et al 1998). Such large scale transient expression employs the transformed human embryonic kidney (HEK293) cells and those engineered to express the Epstein-Barr Virus (EBV) nuclear antigen-1 (EBNA-1).

As such, there is a need for an improved mammalian expression system, which can be used for the production of proteins, in particular recombinant therapeutic proteins and can also be useful in human gene therapy models. Since rodent cells (eg. CHO, BHK, NS0) are routinely used to produce recombinant protein therapeutics, it would be beneficial to have an expression system capable of plasmid replication and retention at work in these cells. The ability to quickly produce recombinant proteins early in product development phase in the same host cell type that would likely be employed for the final bioprocess would clearly be advantageous.

There is also a need for an expression system having enhanced transfection efficiencies, which result in greater recombinant protein expression. Furthermore, there is also a need for cloning/expression vectors that are capable of episomal replication and long-term stable episomal maintenance in mammalian cells.

It is an object of the present invention to overcome or ameliorate at least one of the disadvantages of the prior art, or to provide a useful alternative.

SUMMARY OF THE INVENTION

According to a first aspect, the present invention provides a protein expression system comprising a rodent cell, the rodent cell comprising a gene encoding polyoma large T antigen (PyLT) or a functional equivalent thereof.

According to a second aspect, the present invention provides a protein expression system comprising a rodent cell and a vector, the vector comprising a polyoma origin of DNA replication or a functional equivalent thereof, wherein said cell is suitable for expression of a protein of interest.

According to a third aspect, the present invention provides a protein expression system comprising a rodent cell, the rodent cell comprising a gene encoding polyoma large T antigen (PyLT) or a functional equivalent thereof, and/or a gene encoding EBV nuclear antigen-1, EBNA-1 or a functional equivalent thereof.

It will be clear to the skilled addressee that when mention is made of a cell 'comprising' a gene, the gene may be within the genome of the cell or vector borne.

In one embodiment the protein of interest is a therapeutic protein. In another embodiment the protein of interest is a monoclonal antibody. In a further embodiment, the protein of interest is suitable for use as a vaccine.

According to a fourth aspect, the present invention provides a rodent cell that constitutively expresses large T antigen protein or a functional equivalent thereof.

Accordingly, in a fifth aspect, the present invention provides an expression system comprising a rodent cell, wherein the rodent cell comprises (a) a vector comprising a gene encoding a protein of interest, (b) means to initiate DNA replication of the vector and (c) the oriP and EBNA-1 gene of Epstein Barr Virus family (EBV) or functional equivalents thereof.

Preferably the expression system is a stable episomal replicating system.

It will be clear to the skilled addressee that in the context of the present application, the term "stable" refers to expression of a desired protein beyond 48 hrs. Preferably, the replication and retention of the plasmid expressing the protein of interest lasts for greater than three weeks.

Preferably, DNA replication is initiated by interaction of large T antigen or a functional equivalent thereof with a polyomavirus origin of replication or functional equivalent thereof. More preferably, large T antigen or a functional equivalent thereof is expressed from a gene integrated into the genome of the rodent cell. Without wishing to be bound by theory, the expression of large T antigen or a functional equivalent thereof in the rodent cell may assist in translocating DNA into the nucleus of the rodent cell.

It will be clear to the skilled addressee that the means for initiating DNA replication in the rodent cell may be either transiently or constitutively expressed in the rodent cell.

It will be clear to the skilled addressee that the EBNA-1 gene or functional equivalent thereof may be expressed from a gene integrated into the genome of the rodent cell, or it may be expressed transiently within the rodent cell.

Preferably the expression of the large T antigen or functional equivalent thereof provides the rodent cell with functional benefits. Such benefits include, but are not limited to, an increase in transfection efficiency; enhanced expression of the gene encoding the protein of interest; the ability of the rodent cell to grow as a single cell suspension culture in protein-free medium; and resistance of the cell towards the onset of apoptosis.

According to a sixth aspect, the present invention provides an expression vector for use in a rodent expression system, the expression vector comprising one or more viral elements, wherein said elements are derived from polyoma virus and/or Epstein-Barr Virus (EBV) and include at least one viral origin of DNA replication.

Preferably, the viral elements comprise the polyomavirus origin of replication (oriPV) and/or the EBV origin of replication and/or the nuclear antigen, EBNA-1 of EBV.

Preferably, the vector is capable of episomal replication and long-term stable episomal maintenance in the rodent cell.

According to a seventh aspect, the present invention provides a method for producing a protein of interest comprising culturing a rodent cell, the rodent cell comprising (a) a gene encoding the protein of interest on a vector, (b) means to initiate DNA replication of the vector, and (c) one or more viral elements derived from Epstein Barr Virus family (EBV), under conditions promoting expression of said protein, and recovering said protein.

According to an eighth aspect, the present invention provides a method for producing a recombinant protein, comprising culturing a CHO-K1 cell comprising a gene encoding Polyoma Large T antigen (PyLT) or a functional equivalent thereof and an expression vector according to the invention, under conditions promoting expression of said protein, and optionally, recovering said protein.

According to an ninth aspect, the present invention provides a protein produced according to the method of the invention.

According to a tenth aspect, the present invention provides a pharmaceutical composition comprising a protein produced according to the method of the invention, and a pharmaceutically acceptable carrier.

According to an eleventh aspect, the present invention provides a host cell transformed with a vector according to the invention.

Preferably, the host cell is of rodent origin and includes but is not limited to CHO cells.

According to a twelfth aspect, the present invention provides a method of increasing resistance to apoptosis in a rodent cell comprising expressing polyoma large T antigen or a functional equivalent thereof in the cell.

According to a thirteenth aspect, the present invention provides a method of maintaining a vector in episomal form in a rodent cell comprising inclusion on said vector of an EBV origin of replication or a functional equivalent thereof and/or the nuclear antigen, EBNA-1 of EBV, or a functional equivalent thereof.

According to a fourteenth aspect, the present invention provides a protein expression system comprising a rodent cell, the rodent cell comprising a gene encoding polyoma large T antigen (PyLT) or a functional equivalent thereof, wherein the rodent cell is not a CHO cell.

It will be clear to the skilled addressee that the present invention may also include one or more of the features commonly found in cloning and expression vectors. Such components may include, but are not limited to, a selectable marker (e.g. a gene encoding for antibiotic resistance), multiple cloning sites (a polylinker region) to allow easy subcloning of the fragments into other vectors, a bacteriophage origin of replication to allow production of single stranded copies of the cloned product, and a gene spanning the cloning site which creates an easily detectable phenotype for identification of host cells carrying vectors with inserts (e.g. Lac-Z.alpha.fragment or EGFP) (Sambrook et al. 2001).

In the context of the present invention, the term "protein of interest" includes any peptide or protein. Accordingly, the term includes, but is not limited to, insulin, alpha interferon, hepatitis B surface antigen, GM-CSF, G-CSF, blood clotting factor VIII, erythropoietin, streptokinase, human growth hormone, relaxin, rennin, the interleukins, tumor necrosis factor and follicle stimulating factor.

In the context of the present invention, the term "rodent" includes, but is not limited to, mouse, hamster, beaver, guinea pig, rat, gerbil, capybaras, porcupine, chinchilla, chipmunk, lemming, marmot, gopher, or squirrel.

In the context of the present invention, the term "functional equivalent" includes, but is not limited to, an element that differs from the wild-type by virtue of single or multiple nucleotide deletions, insertions, or mutations that do not, either alone or in combination, deprive the element of its functionality for the purposes of the invention. The term "functional equivalent" also includes elements that are phylogenetically related to the viral elements exemplified in the specification and thereby share functionality or, elements that are not phylogenetically related to the viral elements exemplified in the specification but that perform the same function as those elements exemplified in the specification.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

A. pBK-CMV-LT: Expression plasmid encoding Py large T antigen. The CMV promoter drives expression of Py LT. The Kan/Neo gene confers resistance to G418 in mammalian cells and to Kanamycin in bacterial cells.

B. pGEM-T-PyOri: was constructed by PCR amplification of Py ori using ClaI restriction ends. PCR amplification with Taq DNA polymerase A at the termini allows one-step cloning of PCR fragment into pGEM-T-Easy vector.

C. pEBV (A) and pEBV-d2EGFP: The commercial vector pCEP4 was renamed pEBV in this study. It encodes the gene EBNA-1 and the origin of DNA replication named OriP of the Epstein-Barr virus.

D. pPyOri and pPyOri-d2EGFP was constructed by cloning PyOri into the vector of pEBV previously digested to remove EBNA1 and OriP. This vector represents a positive control for episomal replication in CHO-T cells.

E. pEBV-PyOri and pEBV-PyOri-d2EGFP: Expression vector constructed by cloning PyOri in to pEBV.

F. pBasic and pBasic-d2EGFP: pBasic was constructed from the parent plasmid pEBV by deleting EBNA1 and OriP.

G. pPyOriLT: Polyomavirus Large T antigen and the Py origin were isolated from pPyLT-1 (ATCC) and pPyA3-1 (ATCC) respectively and cloned into pNK, a proprietary vector encoding EGFP reporter (Bailey et al. 1999).

Figure 1A:
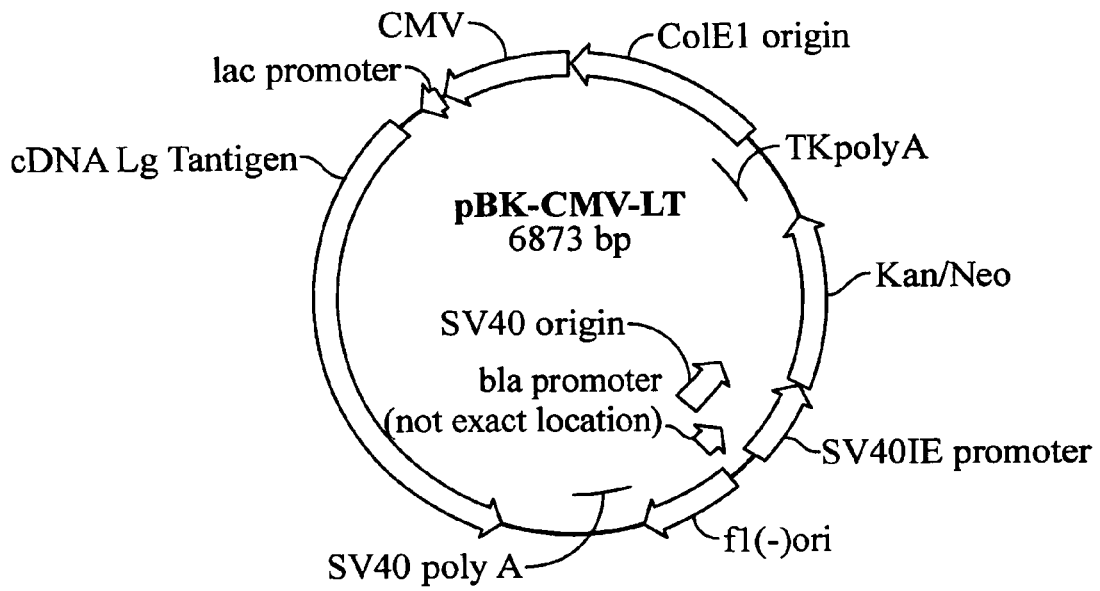
FIG. 1: Plasmids vectors used in this study.
Figure 1B:
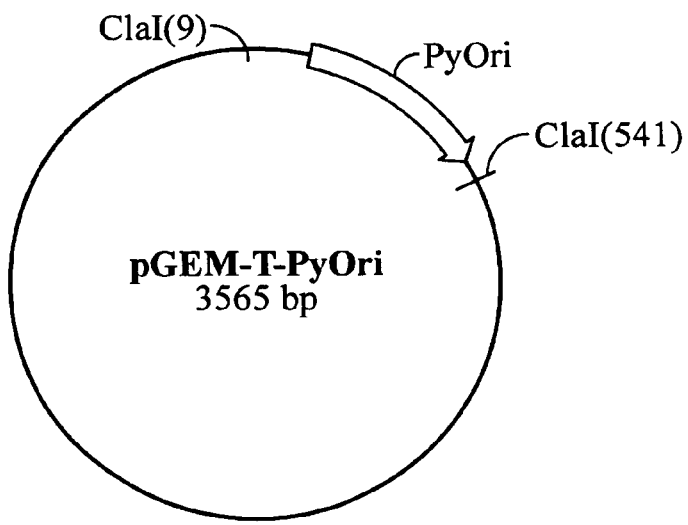
Figure 1C:
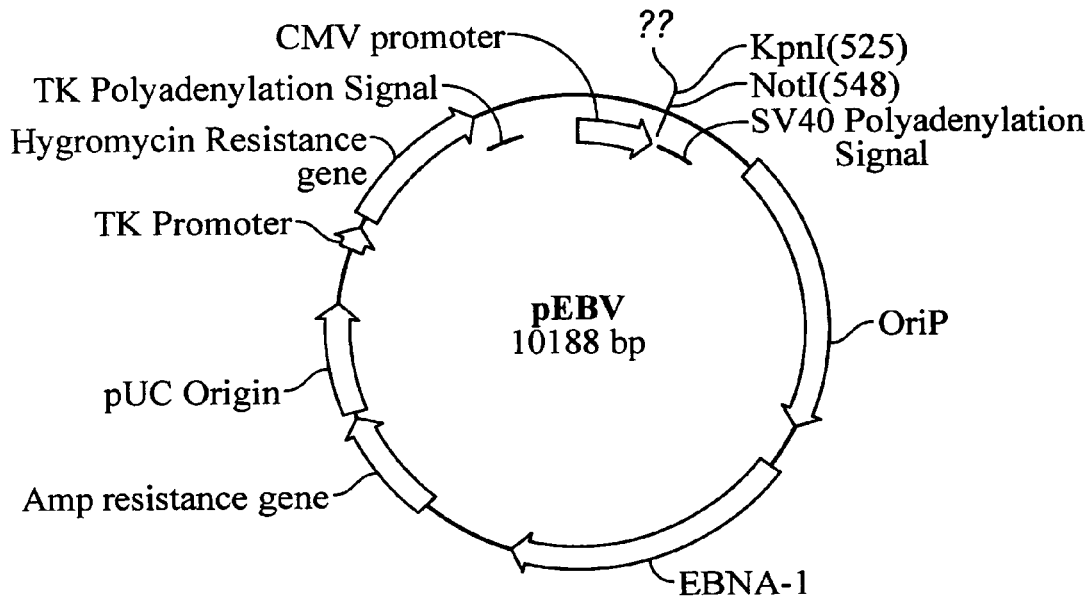
Figure 1C:
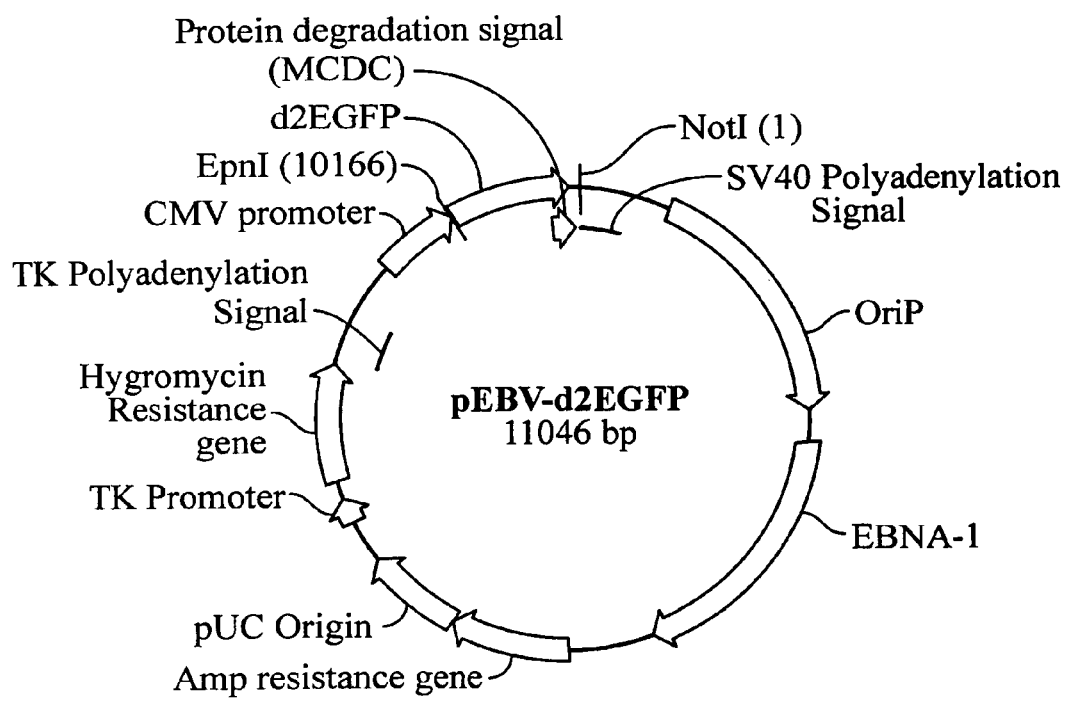
Figure 1D:
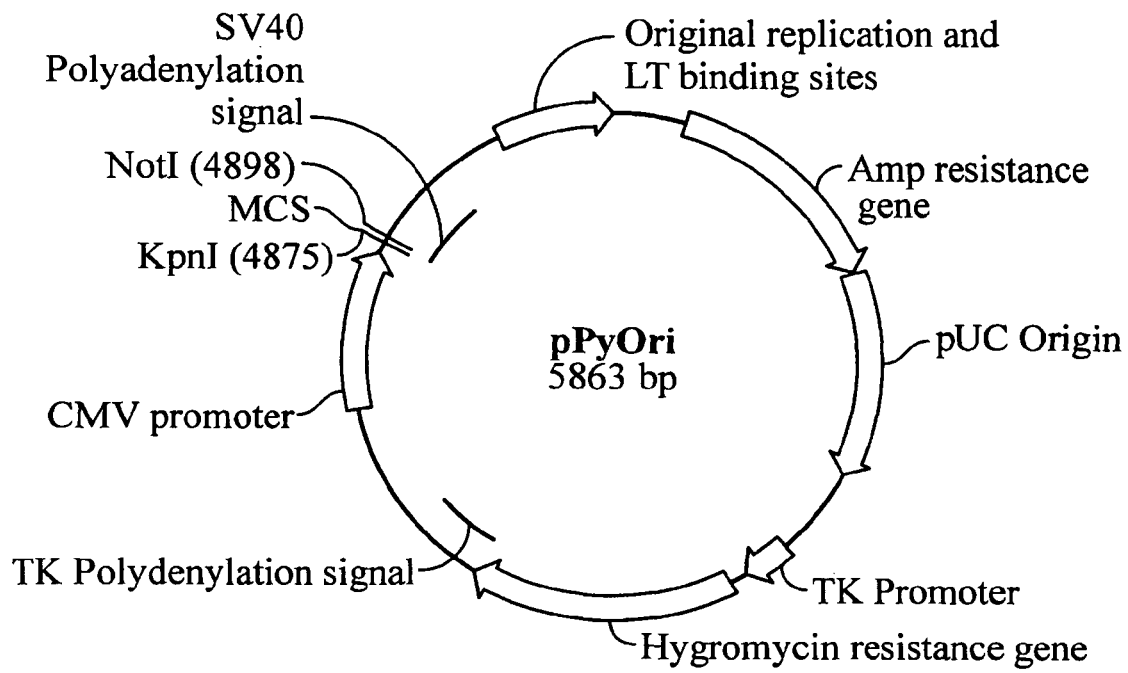
Figure 1D:
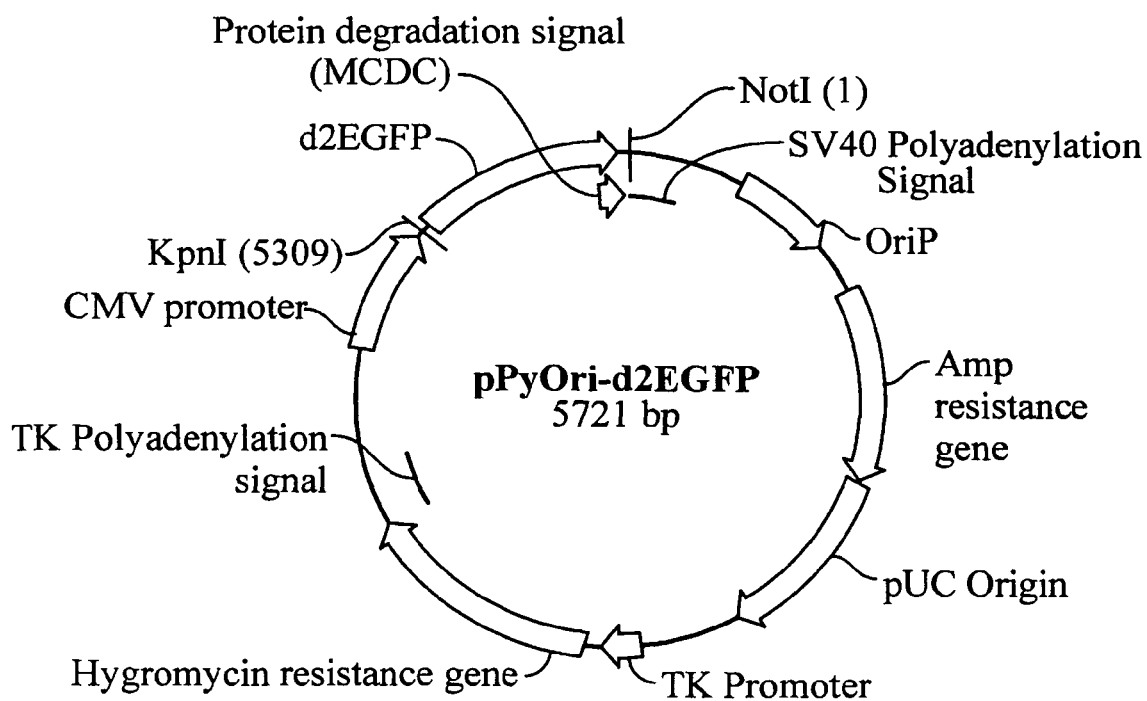
Figure 1E:
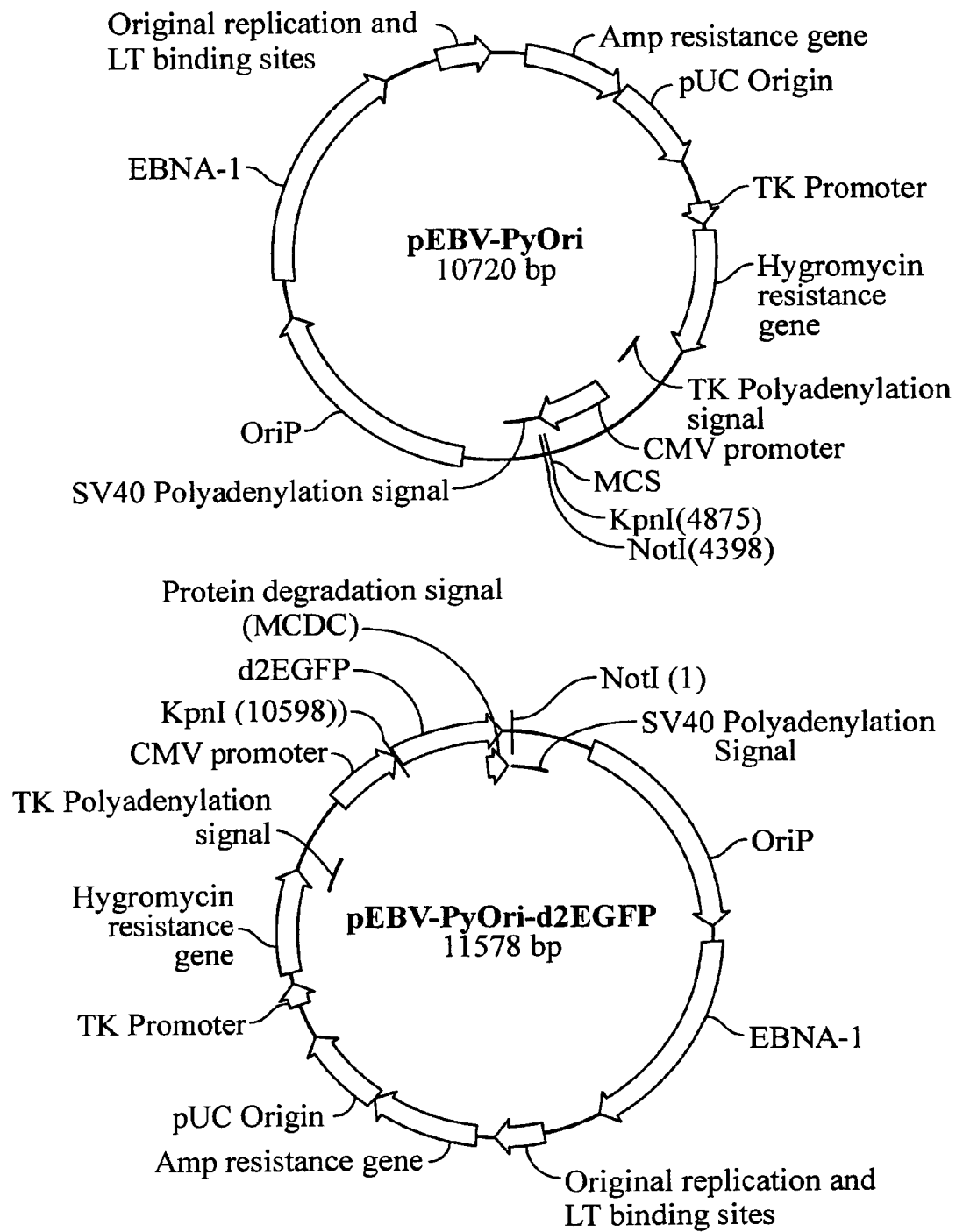
Figure 1F:
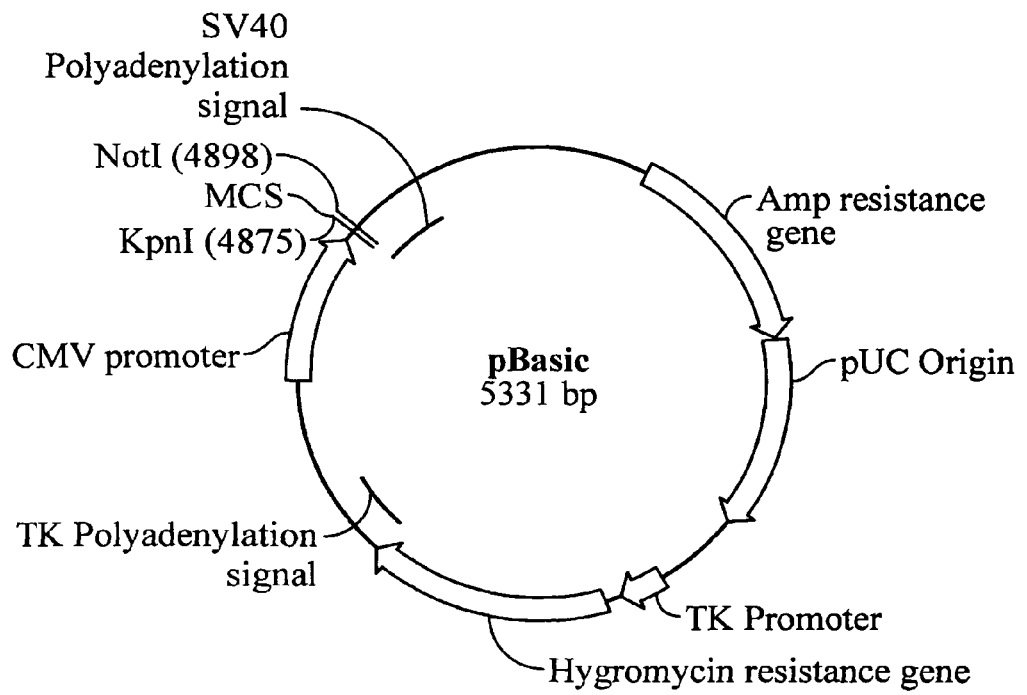
Figure 1F:
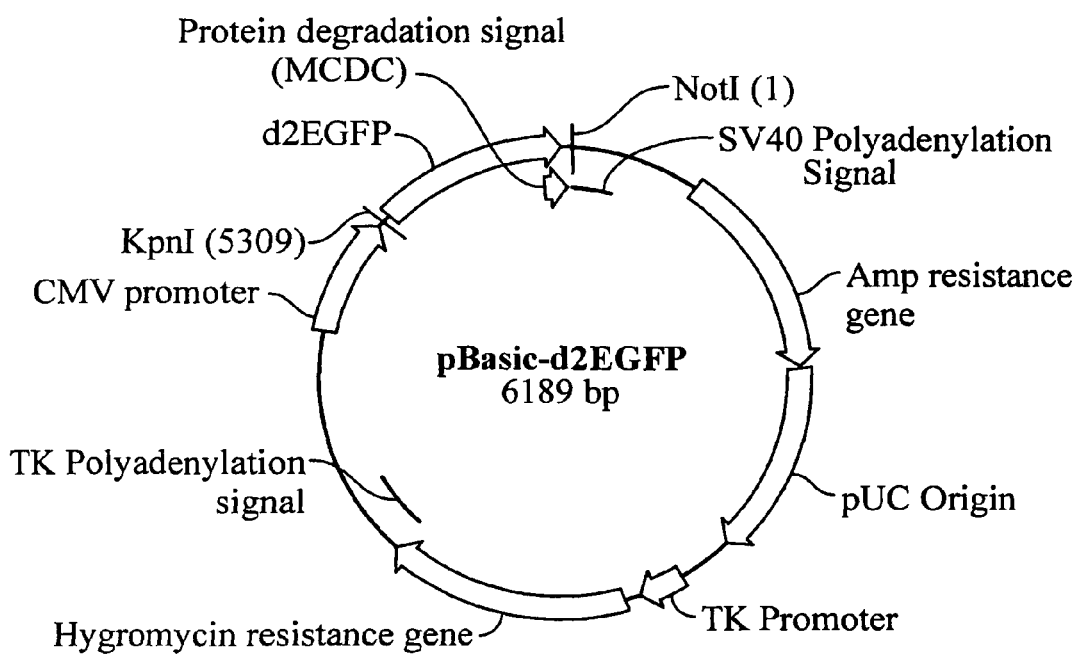
Figure 1G:
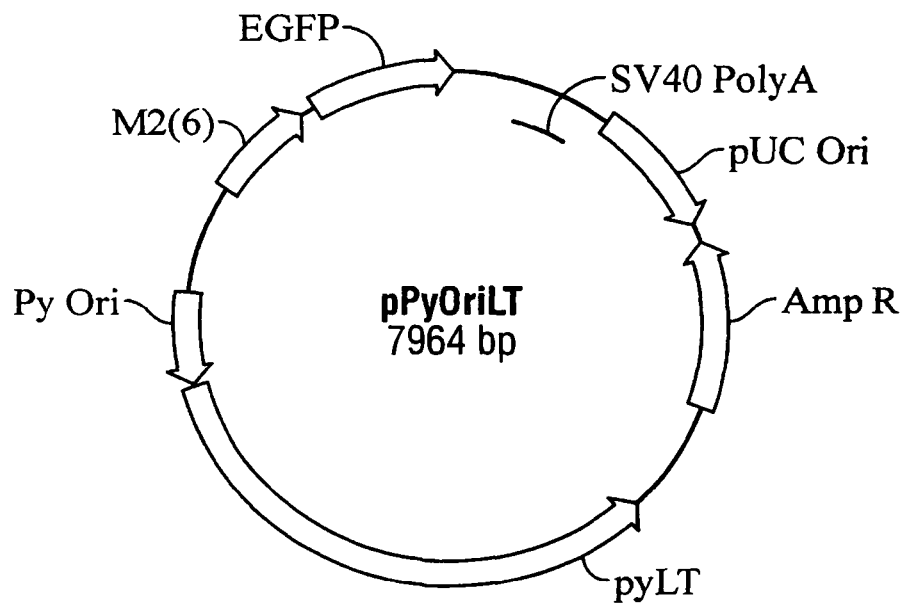
Figure 2A:
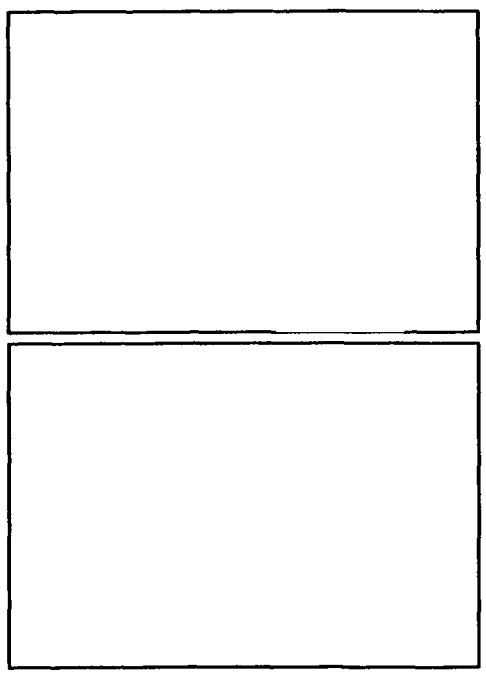
Figure 2B:
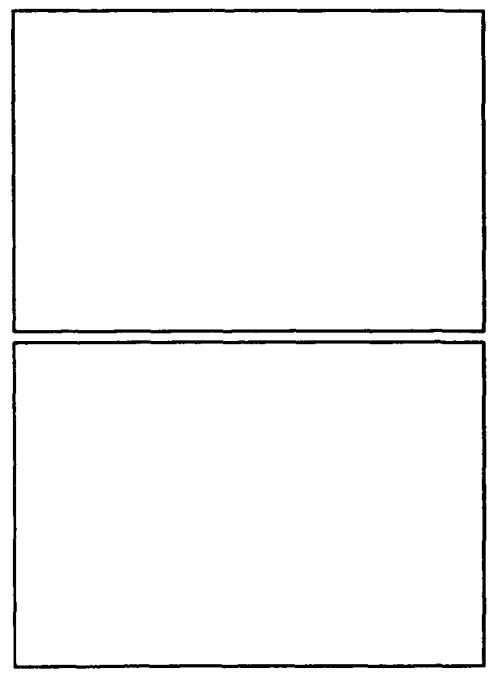

FIG. 2: Immunoflourescence detection of Py large T antigen in CHO cells transfected with pBK-CMV-LT: untransfected CHOK1 (A), CHOK1 cells transfected with pBK-CMY-LT (B). Cells were observed under light microscope (top) and under UV (bottom).

Figure 3:
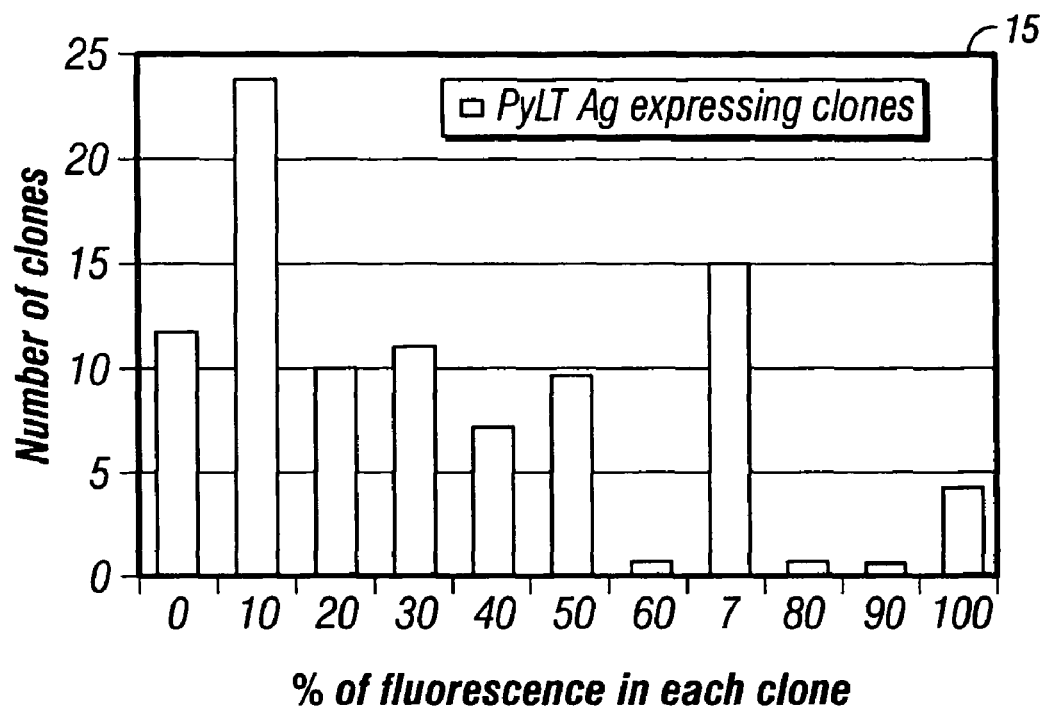

FIG. 3: Frequency distribution of large T antigen expressing CHO-T clones: 92 clones were analysed by immunoflourescence staining for expression of Py large T antigen. Large T expression is noted by the % fluorescence in a defined area (8×12 square cm).

Figure 4:
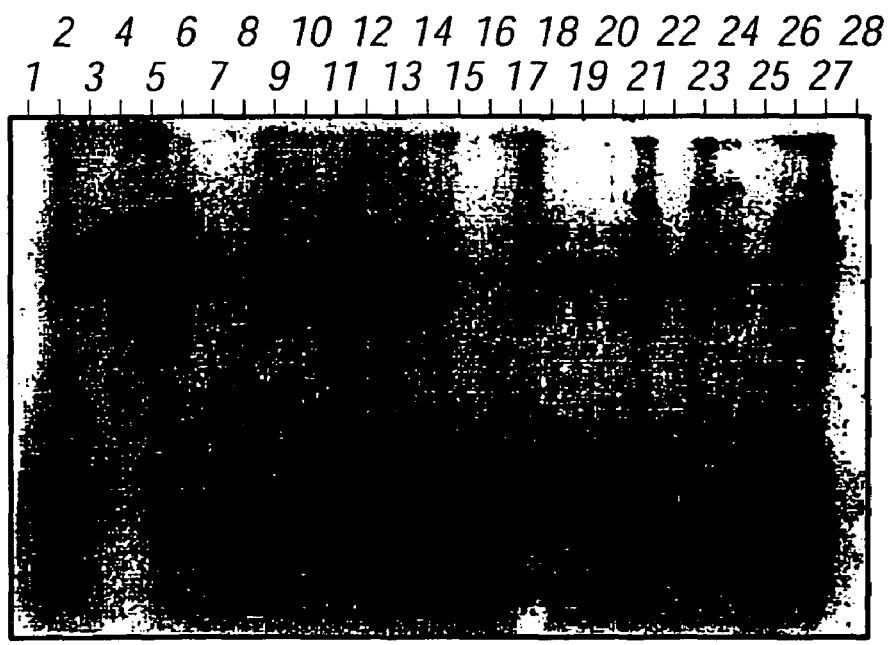

FIG. 4: Southern blot analysis of plasmid replication: The reporter plasmids (5 ug of pNK-Ori-EGFP) was transfected into CHO-T clones, 2.5 ug of pNK-Ori-EGFP and 2.5 ug of pCMV-large T antigen are co-transfected into CHOK1 (+Ve control for transient replication), 5 ug of pPoly-M2.6-EGFP was transfected into CHOK1 ($2^{nd}$+Ve control). 48 hr post transfection low molecular weight DNA was extracted by the method of Hirt extraction. The state of methylation of pNK-Ori-EGFP and pPoly-M2.6-EGFP is measured as an indirect assay of replication by digestion with both DpnI and SpeI after which Southern blot hybridisation was performed with the use of p32 labelled EGFP probe. The mammalian replicated pNK-Ori-EGFP and pPoly-M2.6-EGFP DpnI-resistant plasmids appear as linear plasmids because the plasmids contain one SpeI site, the bacterial replicated pNK-Ori-EGFP and pPoly-M2.6-EGFP DpnI-sensitive plasmids appear as small fragment because the plasmids contain more than one DpnI site. In the above Southern blot lane 1. Control for Bacterial replicated plasmid (pNK-Ori-EGFP plasmid digested with DpnI and SpeI: lanes 2 to 4. Control for Mammalian replicated plasmids loaded at different concentrations (pNK-Ori-EGFP plasmid digested with SpeI, lane 2. 25 ng, lane 3. 50 ng and lane 4. 75 ng); Clone P2-H8, lane 5; Clone P1-C1, lane 6; Clone P1-H2, lane 7; Clone P1-G9, lane 8; Clone P2-G8, lane 9; Clone P2-G6, lane 10; Clone P1-C11, lane 11; Clone P1-G2, lane 12; Clone P2-E12, lane 13; Clone P2-F2, lane 14; Clone P2-F2, lane 15; Clone P1-F2, lane 16; Clone P1-E10, lane 17; Clone P1-F10, lane 18; Clone P2-B7, lane 19; Clone P1-G8, lane 20; Clone P2-D4, lane 21; Clone P1-D2, lane 22; Clone P1-H8, lane 23; Clone P1-B1, lane 24.

Lane 25 Bacterial +Ve control (CHOK1 transfected with pNK-Ori-EGFP); lane 26. Mammalian +Ve control (CHOK1 co-transfected with pNK-Ori-EGFP and pCMV-large T antigen); lane 27. Mammalian +Ve control (CHOK1 transfected with pPoly-M2.6-EGFP); lane 28. −Ve control (CHOK1 ). Replicated DNA bands were quantified using densitometry, BABS, UNSW.

Figure 5A:
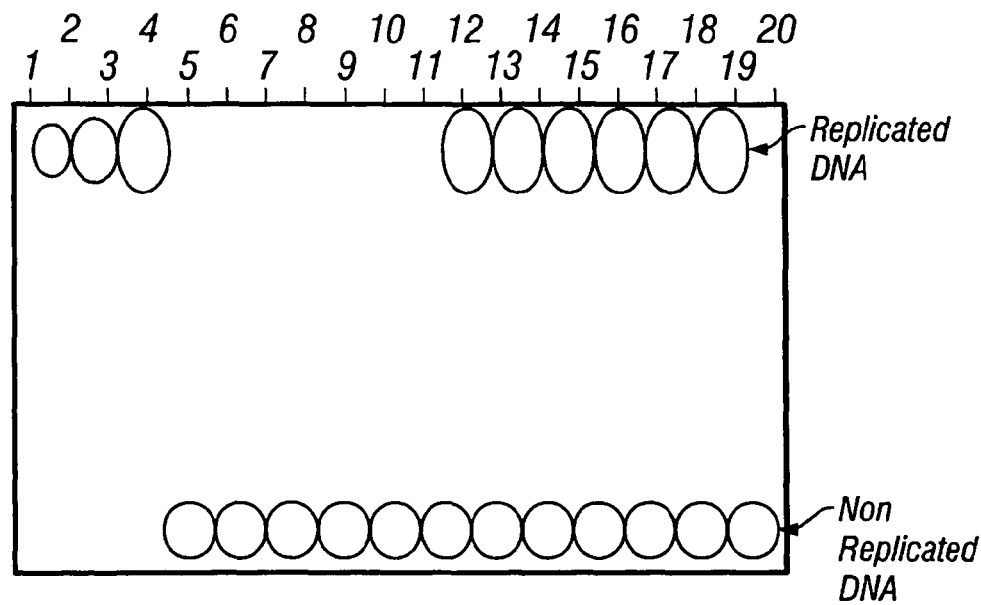
Figure 5B:
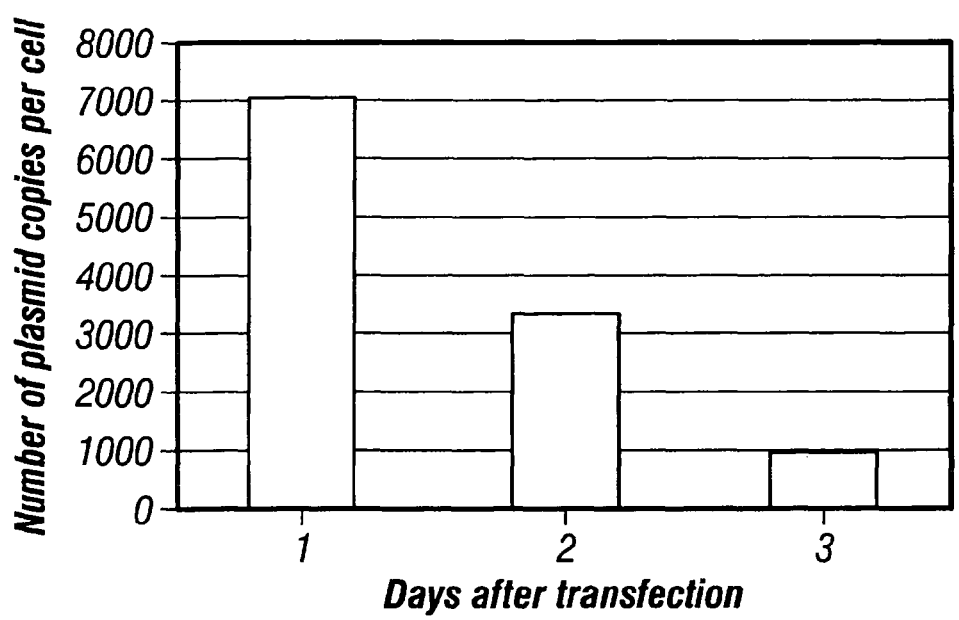
Figure 5C:
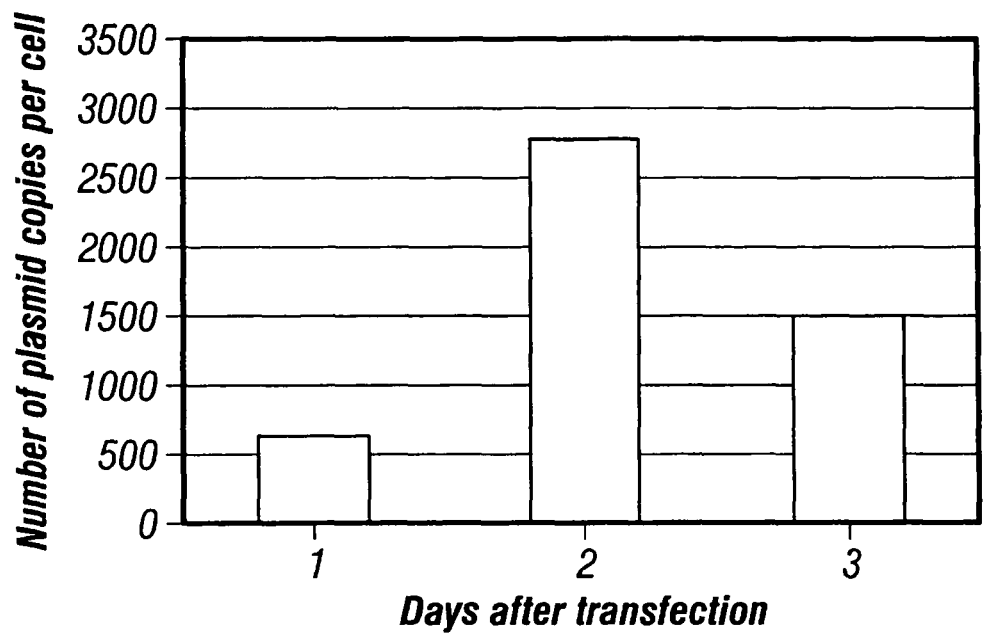

FIG. 5: (1) Southern Blot analysis of Extrachromosomal DNA: Extrachromosomal DNA was isolated using a modified Hirt extraction method (Hirt 1967). Plasmid replication was detected by resistance to cleavage by DpnI, which cleaves only when its recognition site is methylated. DNA purified from a dam+strain of *E. coli* is a substrate for DpnI whereas plasmid DNA which has undergone one or more rounds of DNA replication in mammalian cells is resistant to DpnI cleavage. (2) Plasmid pPyOri-EGFP replication. CHO cells expressing Py large T antigen are capable of supporting replication of pPyOri-EGFP. Unreplicated DNA (A) and replicated DNA (B) were distinguished using the methylation-specific restriction digest of Hirt extracted DNA as described in Materials and Methods.

Figure 6:
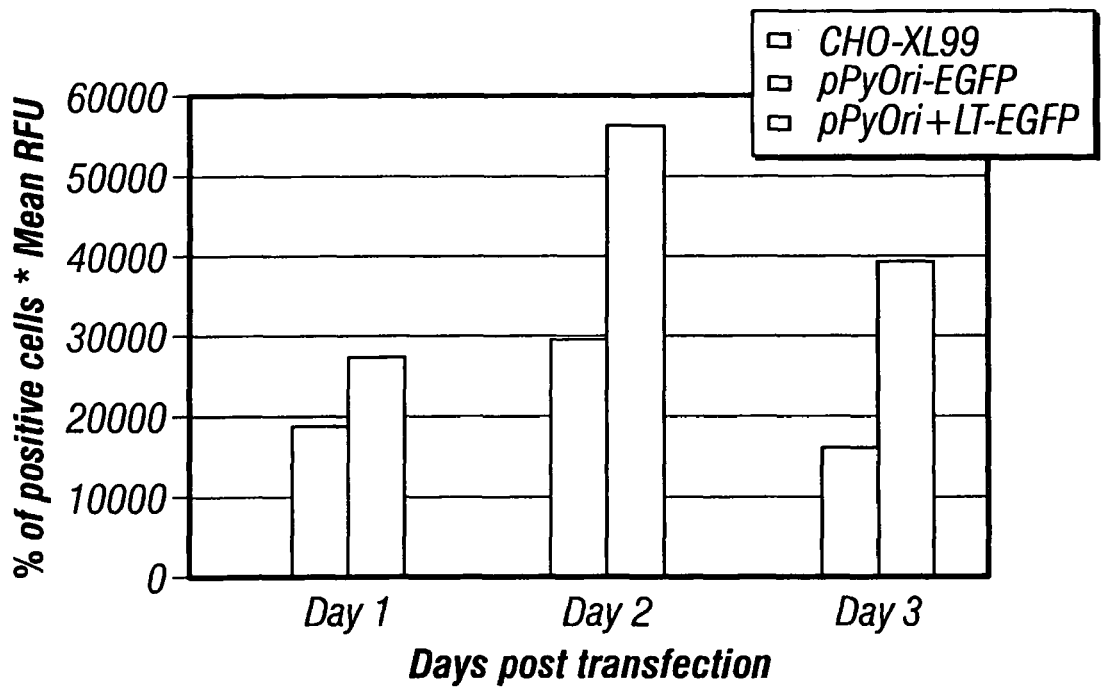

FIG. 6: EGFP expression in transfected CHO cells in the presence and absence of Py large T antigen. EGFP expression is defined as the percentage of fluorescent cells multiplied by their mean relative fluorescent units (RFU).

Figure 7A:
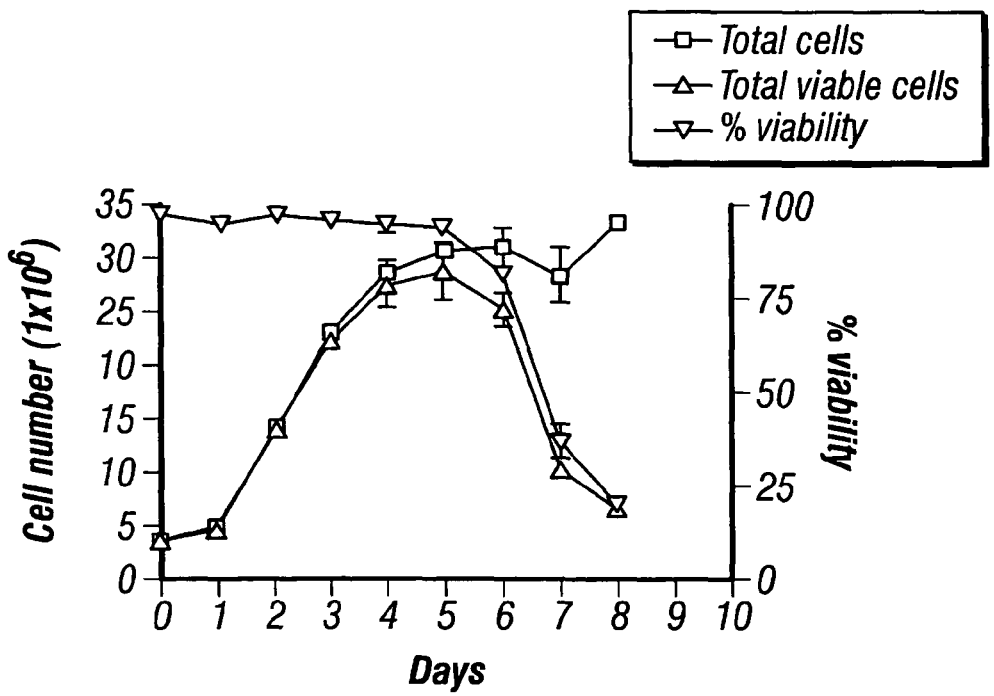
Figure 7B:
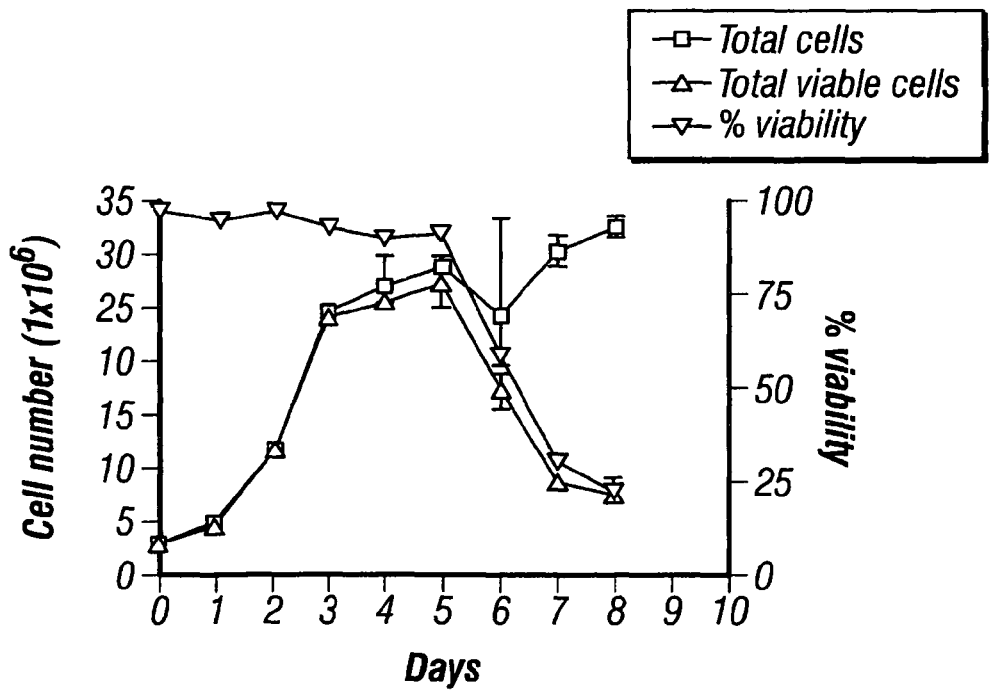

FIG. 7: Growth kinetics: Growth kinetics of CHO-T (A), and CHOXL99 in Excell302 media (B). Batch culture is carried out in a 250 ml spinner with 50 ml's of culture. Cells are seeded at $3×10^5$ cells/ml Excell302 media and cell counts performed every day. From this study CHO-T cells had a doubling time to 21.23 hr with a peak cell density of $2.85×10^6$ cells/ml. CHOXL99 had a doubling time of 20.01 hr with a peak cell density of $2.75×10^6$ cells/ml.

Figure 8:
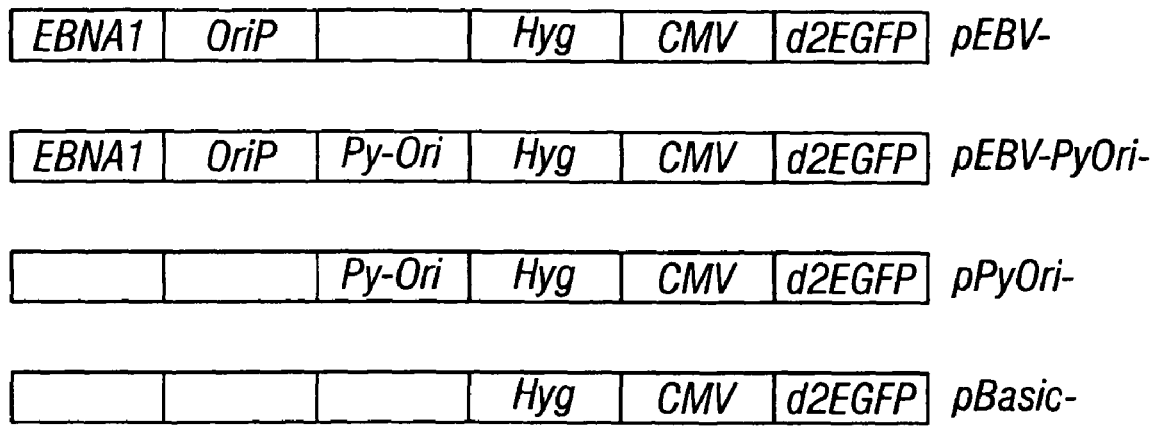

FIG. 8: Vectors constructed to compare expression efficiencies in CHO cells. Detailed plasmid maps are shown in FIG. 1.

FIG. 9

A. GFP Expression in CHO-T cells. Facs analysis revealed that the number of cells expressing GFP when transfected with the hybrid plasmid pEBVPyOri-d2EGFP was significantly greater than CHO-T cells transfected with pPyOri-d2EGFP, pEBV-d2EGFP or pBasic-d2EGFP.

B. Mean GFP Expression over time. In a transfected pool of CHO-T cells, (CHO cells expressing polyomavirus large T antigen) the number of cells expressing GFP using pEBVPy-Ori-d2EGFP increases in number where other pools show a decrease in number and expression.

FIG. 10: Long term stable episomal maintenance study with selection (% of d2EGFP expressing cells): CHO-T (A), CHOXL99 (B) and HEK293 (C) Cells are transfected with 5 ug of pEBV-d2EGFP, pPyOri-d2EGFP, pEBV-PyOri-D2EGFP and pBasic-d2EGFP plasmids. 48 hrs post transfection cells are selected with hygromycin (400 ug/ml). FACS analysis performed to measure the % of GFP expressing cells.

FIG. 11: Recombinant protein production in CHO-T cells transiently transfected with non-replicating and replicating expression vectors. In 6-well plates, CHO-T cells (A) and CHOXL99 cells (B) were transfected with expression plasmids as indicated. Following transfection, cells were seeded at a density of $5×10^6$ cells/ml in a total volume of 2 ml. Cell counts were determined using a haemocytomer and viability was determined using the trypan blue method. HGH concentration was determined using ELISA (Roche).

Figure 12A:
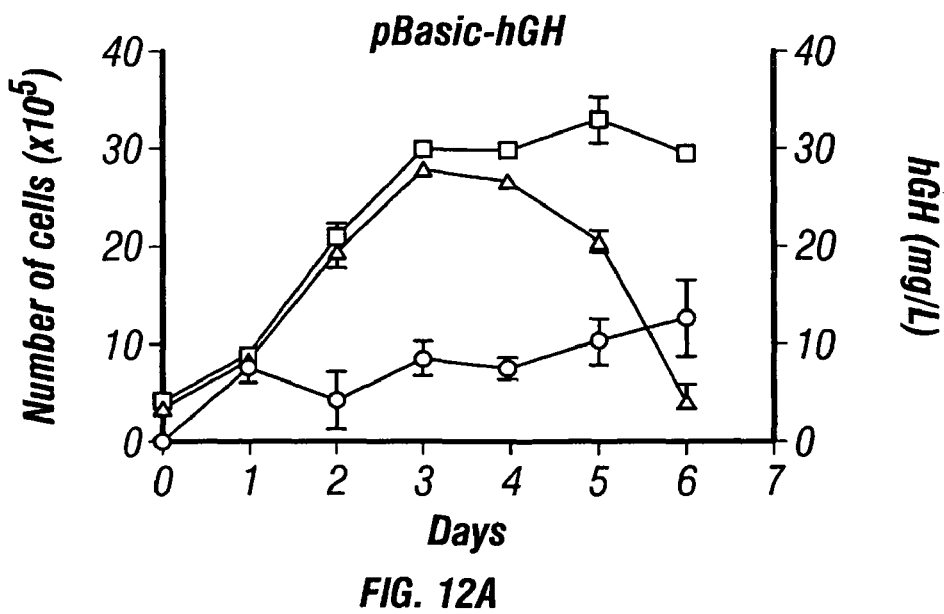
Figure 12B:
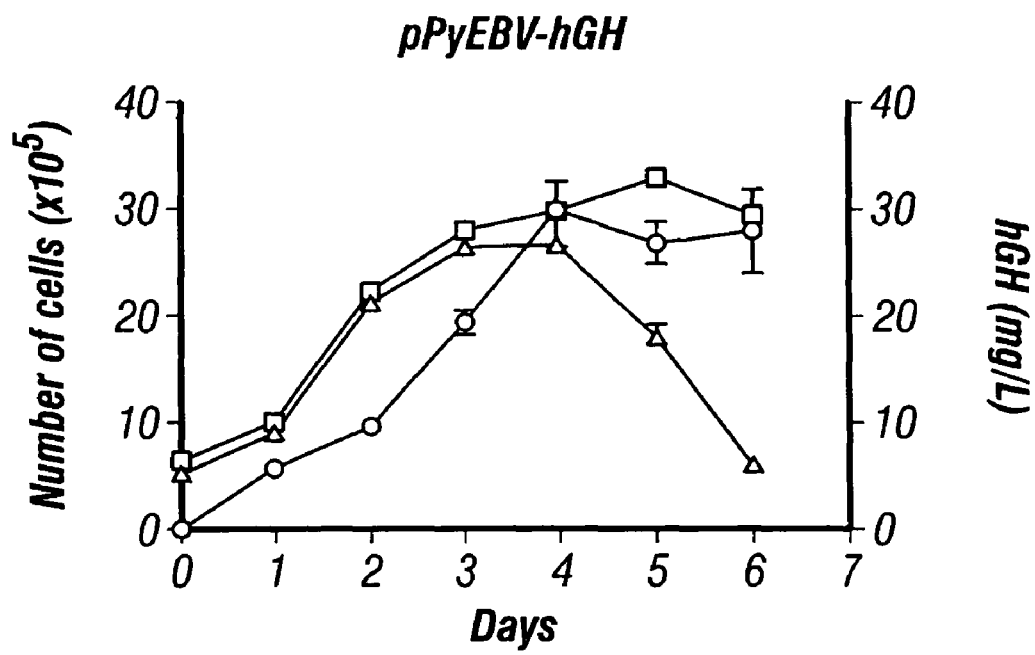

FIG. 12. Batch study or recombinant protein production in CHO-T transfected with A) pBasic- and B) pPyEBV vectors encoding hGH. Cells were transfected and seeded into 100 ml spinner flasks. Cell counts were determined using a haemocytometer and viability was determined using the trypan blue method. Product concentration was determined using hGH ELISA kit (Roche). Squares: total cell numbers; triangles: total viable cell numbers; circles: hGH yield.

Figure 13A:
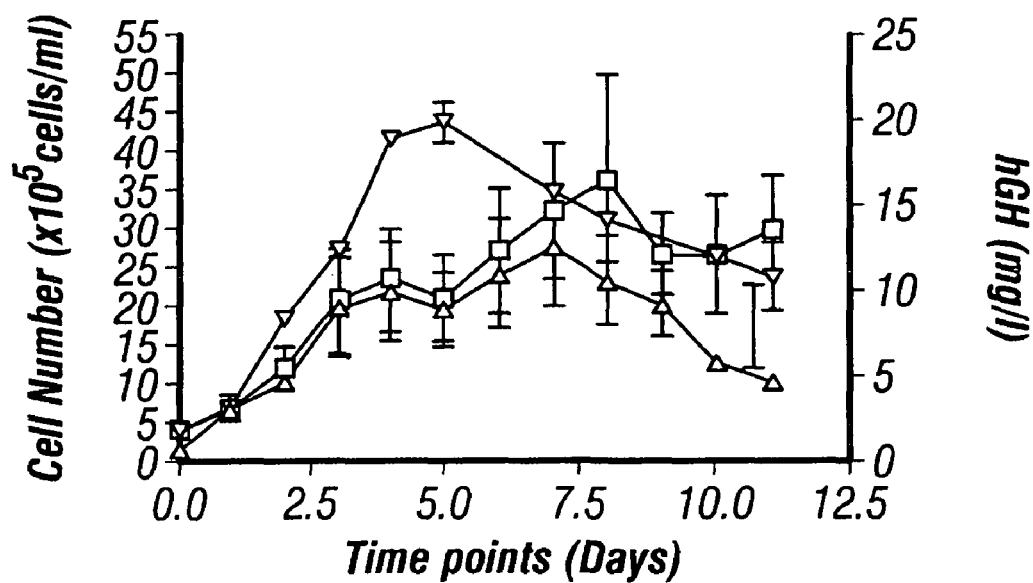
Figure 13B:
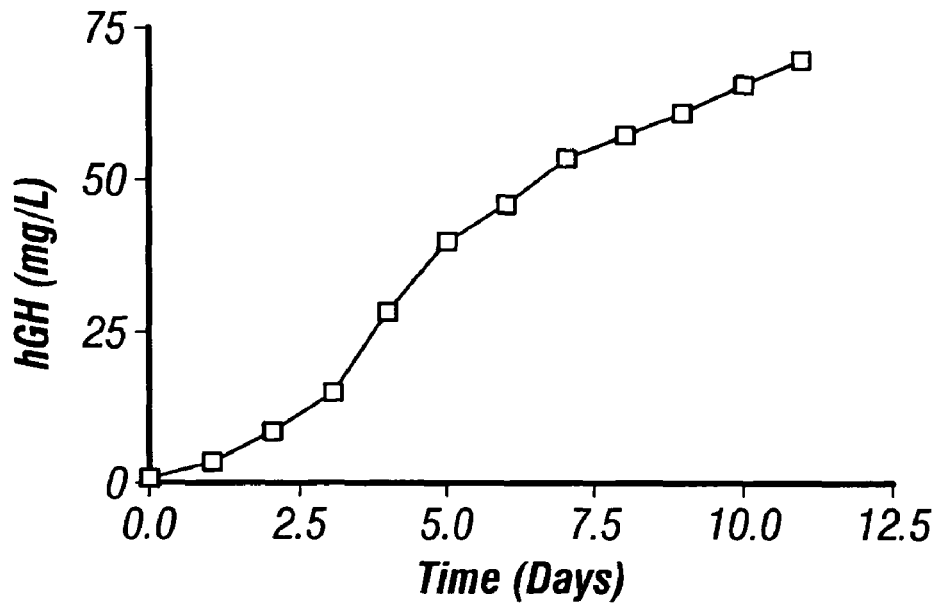
Figure 13C:
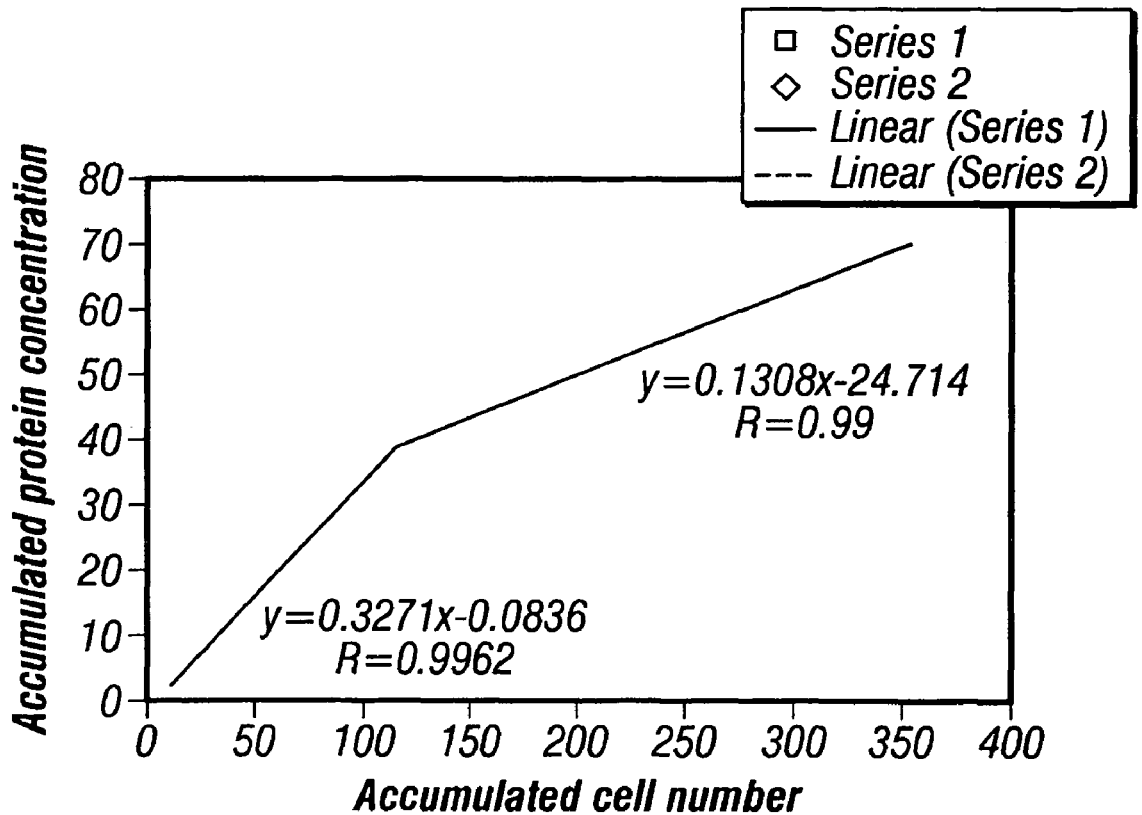

FIG. 13: HGH productivity in CHO-T cells transfected with pPyEBV/PyOri-HGH. A. Following transfection, cells were seeded in 100 ml spinner flasks at density of $5 \times 10^5$ cells/ml in a total volume of 50 ml. Cell counts were determined using a haemocytomer and viability was determined using ELISA (Roche). B. Accumulated protein concentration over time. C. Specific productivity was determined by calculating the change in accumulated protein concentration divided by the change in accumulated cell number. Calculated specific productivity during batch run. Maximum specific productivity was determined.

Figure 14:
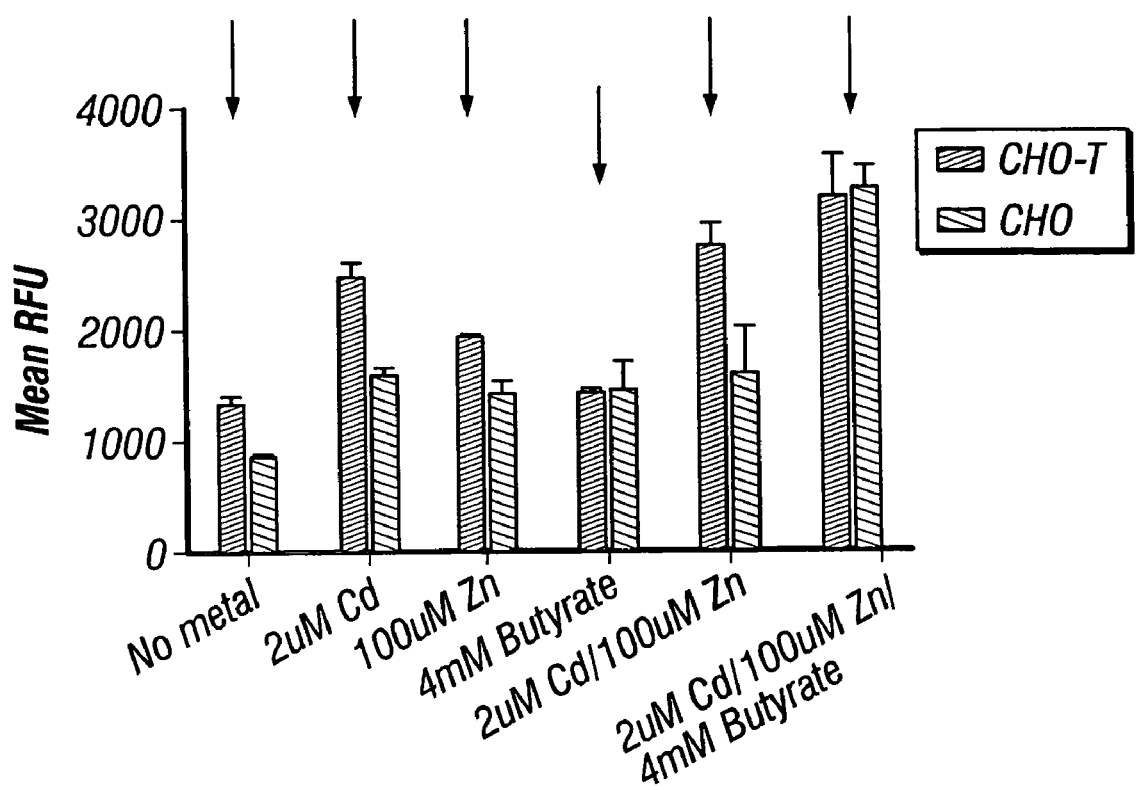

FIG. 14: Large T expression in CHO cells mimics effects of sodium butyrate. CHO and CHO-T cells were transfected with the vector pNK-d2EGFP. The pNK vector allows for the selective activation of expression of the protein of interest encoded by the vector by the addition of metal. CHO-T cells, expressing the large T antigen mimicked the effect of sodium butyrate by activating EGFP gene expression.

DESCRIPTION OF THE INVENTION

Preferred embodiments of the invention will now be described by way of example only with reference to the accompanying figures.

The examples below describe the development of a mammalian expression system capable of long-term transient production of recombinant protein in Chinese hamster ovary (CHO) cells. The expression system comprises 1) a derivative of the parental CHO-K1 cell line having in its genome the large T antigen gene of Py (Py), into which is transfected 2) a DNA expression vector consisting of one or more viral elements for episomal replication and/or stable plasmid maintenance. The CHO-K1 cell line expressing Py large T antigen, named CHO-T was developed for the large-scale transient production of recombinant therapeutic proteins. Several advantages of the CHO-T cell line make it particularly suited for the production of therapeutic proteins. CHO-T is a fully characterized derivative of CHO-K1. It grows in single-cell suspension in protein-free media. Due to the constitutive expression of Large T and its ability to initiate Py ori-containing plasmid DNA replication, the cell line exhibits enhanced transgene expression and protein production. Green fluorescent protein (GFP) and human growth hormone (HGH) were used as reporter genes to demonstrate transgene expression. Cells were transfected with pPyOri, an expression vector containing the Py origin of DNA replication, or pEBV, an expression vector containing the oriP and EBNA-1 protein of Epstein Barr Virus (EBV) or pEBV-PyOri, a hybrid expression vector containing both Py origin and EBV oriP and EBNA-1. Results indicate that both pPyOri and pEBV-PyOri vectors are capable of episomal replication in CHO-T cells. Prolonged gene expression is evident in cells harbouring the hybrid vector pEBV/PyOriGFP or pEBV/PyOriHGH compared to cells transfected with pPyOriGFP or pPyOri-HGH. The prolonged and elevated gene expression using pEBV/PyOri is a result of a combination of plasmid replication, episomal maintenance and plasmid segregation during cell division. The Py-based expression vectors and CHO-T cells provide efficient CHO expression systems for the production of recombinant protein. The hybrid expression system comprising the expression vector pEBV/PyOri and CHO-T cells is particularly useful for the large-scale transient production of recombinant protein in industrial applications.

EXAMPLE 1

Materials and Methods
Cells and Media
CHO-K1 (ATCC CCL 61) were grown in DMEM:COONS F12 containing 10% FBS. CHO-T cells were adapted to suspension growth in serum-free medium (Excell302; JRH Biosciences, Kansas) and protein-free medium (Excell325; JRH Biosciences, Kansas). XL99 cells (a suspension CHO-K1 cell line adapted to growth in suspension in serum-free media (Neil Kitchen 1999)) were grown in Excell302.
NS0-T
NS0 cells (Non-secreting mouse myeloma cells) (ECACC 85110503) were used to transfect plasmid encoding Polyoma virus Large T antigen.
Electroporation of NS0
Electroporation of NS0 cells was carried out using an adapted protocol described by Chu G et al 1987. Briefly, $1-1.5 \times 10^7$ NS0 cells were grown to mid-log phase and electroporated with 10 ug of pBK-CMV-Large-T-Antigen plasmid at 250V using a square wave pulse for 15 ms. Cells were selected 48 hours post transfection in G418 (400 ug/ml).
Lipofection of NS0
Lipofections were carried out using the lipofectamine2000 reagent (Invitrogen) according to the manufacturer's directions. Briefly, concentrations of DNA and lipofectamine2000 were prepared in Optimem media at room temperature and incubated for 5 minutes. The DNA and lipofectamine2000 were combined and incubated together for a further 20 minutes before addition to $5 \times 10^5$ cells suspended in 500 ul in 24 well plates. Cells were then analysed using FACS (Cytomation MoFlo cytometer) after 24 or 48 hours.
Transfection
Transfection quality DNA was prepared using Nucleobond®AX columns (Macherey-Nagel, Duren, Germany). DNA concentrations and purity were independently assayed using analytical gel electrophoresis, restriction enzyme digestions and spectrophotometry.

Suspension cells were transfected as follows: Transfections were carried out in 6 well plates (eg. Iwaki, Tokyo, Japan). Cells in mid log phase were washed with 1×PBS (phosphate-buffered saline: 137 mM NaCl, 2.7 mM KCl, 4.3 mM $Na_2HPO_4.7H_2O$, 1.4 mM $KH_2PO_4$) once and then resuspended at $0.75 \times 10^6$ cells/ml Opti-MEM media. $1.5 \times 10^6$ Cells were transfected with 5 ug of plasmid and 10-15 ul of Lipofectamine 2000® (Life Technology). 12 hr post transfection cells were resuspended in 2 ml of Excell302 media and treated with selection reagents as required.
Isolation of Extrachromosomal DNA and Southern Blot Hybridisation
Cells at mid log phase were washed once with 1×PBS and resuspended at $0.93 \times 10^6$ cells/ml Opti-MEM Media (Life Technology Inc). 2 ml of resuspended culture was then transfected with 5 ug of (plasmid) and 10 ul LF 2000® in a 6 well plate. 6 hr post transfection 2 ml of Excell302 media was added. 24-48 hr post transfection cells were harvested and low molecular weight DNA was isolated according to the Hirt extraction technique (Hirt, 1967). Briefly cells were harvested and washed with 1×PBS then resuspended in 1 ml 0.6% SDS/0.01M EDTA, pH7.5. After incubating this cell suspension at room temperature for 20 min, 250 ul of 5M NaCl was added to the cells and mixed gently. The resulting mixture was then incubated at 4° C. overnight. Supernatant was collected by centrifuging at 15,000 g for 30 min. Supernatant samples were first extracted twice with phenol chloroform and then with chloroform. DNA was isolated by ethanol precipitation and resuspended in 20-30 ul of TE buffer pH8.
Isolation of Extrachromosomal DNA and Replication Assay Extrachromosomal DNA was isolated using a modified Hirt Extraction method (Hirt 1967) at 24, 48 and 72 hr post transfection. Briefly, cells were washed with PBS and incubated with 0.6% SDS (w/v)/10 mM EDTA solution for 20 min. NaOH was then added to a final concentration of 1M and the reaction was allowed to incubate at 4° C. overnight. Samples were centrifuged in an Eppendorf centrifuge for 20 min. Following extraction with phenol:chloroform:Isoamyl alcohol (two times, Sigma Aldrich, St. Louis, Mo., USA) and once with chloroform (Sigma Aldrich), DNA was precipitated with absolute ethanol and then resuspended in TE (10 µl). Hirt-extracted DNA was digested with SpeI and DpnI (New England Biolabs, Beverly, Mass., USA) in 50 mM NaCl, 10 mM Tris-HCl, and 1 mM dithiothreitol at 37° C. for 2 h and electrophoresed on an 0.8% agarose gel for 1 h. Southern hybridisation was carried out according to the method of Ausubel, 1997. Briefly, cells were soaked in depurination solution (0.25 M HCl) for 30 min, denaturating solution (1.5 M NaCl/0.5 N NaOH) for 20 min and neutralization (2M Tris-HCL/2 M NaCl) for 20 min. DNA was then transferred to nitrocellulose membrane in 20×SSC using a vacuum blot apparatus. The membrane was allowed to dry for 30 min at room temperature before baking at 80° C. in a hybridization oven. The membrane was pre-hybridized in (5×SSC/5×Denharts/0.5% SDS, 100 µg/ml salmon sperm DNA (Invitrogen)) at 68° C. for 6 h before addition of $^{32}$P-labelled EGFP probe (Clonetech). After 12 h incubation at 68° C. the membrane was washed once in 50 ml of 2 SSC/0.1%/SDS at room temperature, once with 50 ml of 1×SSC/0.1% SDS at room temperature and once with 0.1%×SSC/0.1% SDS (w/v) at 68° C. for 20 min after which the membrane was exposed to autoradiography film and DNA was quantified using a Biorad-525 densitometer.
Vector construction
pGEM-T-PyOri:

pGEM-T-PyOri was constructed by PCR amplification of the 548 bp Py origin of DNA replication (PyOri) from pPyA3-1 (ATCC) using PyOri-ClaI-AS (antisense) and PyOri-ClaI-S (sense) primers shown in Table 1. Amplified DNA was then cloned into linearised pGEM-T Easy vector (Invitrogen). The pGEM-T-PyOri plasmid map is shown in FIG. 1.

TABLE 1

Primers used to amplify PyOri in pPyA3-1 plasmid

| PyOri-ClaI-AS | 3'actacatcgatcagtctccctcgatgaggtctacta5' (SEQ ID NO: 1) |
| PyOri-ClaI-S | 5'tactcatcgatctacgtatccatgatggtggtggtgagg3' (SEQ ID NO: 2) | pBasic:
pBasic was constructed by digesting pCEP-4 (Invitrogen) with ClaI and religating the fragment lacking EBNA-1 and OriP.
pPyOri:
pPyOri was constructed by isolating and ligating the ClaI fragment (nucleotide 9 to 541) in pGEM-T-PyOri (grown in GM2163$^{(dam-ve)}$bacteria) to pBasic plasmid (grown in GM2163,$^{(dam-Ve)}$bacteria) linearised using ClaI (nucleotide 1) and dephosphorylated with calf intestinal alkaline phosphatase (CIAP).

pPyOriLT:
Polyomavirus Large T antigen and the Py origin were isolated from pPyLT-1 (ATCC) and pPyA3-1 (ATCC) respectively and cloned into pNK, a vector encoding EGFP reporter.
pEBV-PyOri:
pEBV-PyOri was constructed by ligating the ClaI (nucleotide 9 to 541) fragment in pGEM-T-PyOri (grown in GM2163$^{(dam-ve)}$bacteria) to pCEP-4 plasmid (Invitrogen) linearised with ClaI (nucleotide 5939) and dephosphorylated with CIAP.
pEBV-d2EGFP, pPyOri-d2EGFP, pEBV-PyOri-d2EGFP and pBasic-d2EGFP:
pEBV-d2EGFP, pPyOri-d2EGFP, pEBV-PyOri-d2EGFP and pBasic-d2EGFP were constructed by isolating DNA encoding the destablised EGFP protein d2EFGP as a KpnI (nucleotide 889) to the NotI (nucleotide 1806) fragment from pCMV-d2EGFP (Clonetech, USA) and ligating to KpnI (nucleotide 625 in pEBV, 4875 in pPyOri, 4875 in pEBV-PyOri and 4875 in pBasic plsmids) and NotI (nucleotide 648 in pEBV, 4898 in pPyOri, 4898 in pEBV-PyOri and 4898 in pBasic plasmids) digested pEBV, pPyOri, pEBV-PyOri and pBasic plasmids.
pEBV-hGH, pPyOri-hGH, pEBV-PyOri-hGH and pBasic-hGH The DNA sequence encoding for human growth hormone (hGH) was digested from pCBhGH (Bailey et al 2002) and ligated into the KpnI site of pBasic, pPyOri, pEBV-PyOri, and pEBV.
Flow Cytometry Analysis All data presented were gathered on a Cytomation MoFlo cytometer (Cytomation, Fort Collins, Colo.), equipped with Summit 3.0 software and an argon-ion laser operating at 200 mW and tuned to 488 nm in light regulation mode. Forward angle and side-scatter light gating were used to identify viable populations whilst doublets were excluded using forward angle and pulse-width scatter gating. A 525-nm short pass dichroic mirror was used to separate eGFP fluorescence. eGFP emission (whose emission maxima occurs at 508 nm) was detected on FL4 using a 510/23-band pass filter. A comparative analysis was also made using a 555-nm long pass dichroic mirror to reflect eGFP emission to FL1 but there was no statistically relevant difference noted in mean fluorescence intensities using either the 525-nm short pass or the 555-nm long pass dichroic mirrors (data not shown). On occasion a 1.3 ND filter was used to reduce eGFP fluorescence intensity below the 4$^{th}$ log decade. PMT voltages were adjusted to ensure auto-fluorescence associated with untransfected controls described a Gaussian distribution within the first log-decade. Analysis was maintained at an event rate not exceeding 600 cells per second and a total of 20,000 events were acquired per sample. Comparative assessments of mean fluorescence data from treatment samples were made with respect to controls.
Immunofluorescence Staining and Detection of Large T Antigen Expression:

The day before immunofluorescence staining, CHO-T cells were detached with EDTA/PBS and the seeded at 3×10$^5$ cells/well in a tissue culture treated 6 well plate containing sterile 1/1 cm glass cover slip. Once the cells had reached ≧90% confluence they were washed once with phosphate buffered saline (PBS) and fixed with 1 ml of 2% formaldehyde/0.1% Triton×100 for 30 min on ice. Cells were then washed three times with PBS and incubated for 5 min at room temperature between each wash. Cells were blocked using 2 ml 1×PBS/10% FBS for 22 minutes followed by the addition of 25 ul of Ab-1 (monoclonal antibody to Py Large T antigen, 1 ug/ml Oncogene Research Products, Santa Cruz) at room temperature for 1 hr. Cells were washed three times with PBS as described above. Cells were incubated with 25 ul of FITC conjugated ANTI-RAT IgG (Whole molecule) (1:32 dilution) (Sigma), for 1 hr at room temperature in the dark. Cells are washed three times as described above. The cells were then incubated in PBS in the dark until observed under a fluorescent microscope.

HGH Determination and Protein Quantitation

HGH was measured from conditioned media using an ELISA kit (Roche).

EXAMPLE 2

Episomal Replication in CHO Cells

The expression vector pPyOriLT (FIG. 1G) was transfected into CHO cells to demonstrate episomal replication. Accordingly, pPyOriLT contains PyOri and encodes PyLT, the two viral elements necessary and sufficient to initiate plasmid DNA replication in the presence of permissive CHO cellular factors. Plasmid DNA replication was monitored over 3 days. Low molecular weight DNA was purified from transfected cells according to the Hirt extraction technique as described above (FIG. 5(1)). Plasmid replication was detected by resistance to cleavage by DpnI, which cleaves only when its recognition site is methylated. DNA purified from a dam+strain of E coli (lanes 1 to 4) is a substrate for DpnI (lane 5) whereas plasmid DNA which has undergone one or more rounds of DNA replication in mammalian cells is resistant to DpnI cleavage (lanes 11-20). As shown in FIG. 5(2), the total amount of non-replicated DNA (DpnI-sensitive) drops rapidly from 7000 copies per cell following transfection to under 1000 copies per cell on day three. These results indicate that although CHO cells support the episomal replication of PyOriLT, the rapid decline in plasmid DNA soon after transfection limits the duration of transient gene expression to 3 to 4 days.

EXAMPLE 3

(a) Development of CHO-T Cell Line

The cDNA for Py large T antigen was obtained from ATCC and cloned into the expression vector pBK-CMV (Clonetech). The expression plasmid pBK-CMV-LT (FIG. 1) was used to transfect CHO-K1 (ATCC, CCL61). Cells were selected in G418 (400 ug/ml) for two weeks. Expression of Py Large T antigen was confirmed by immunofluorescence staining as shown in FIG. 2. Individual cells were isolated by fluorescence-activated cell sorting (FACS) using a MoFlo cytometer (Dako-Cytomation, Fort Collins, Co., USA). Several clones were isolated which had varying levels of large T antigen as indicated in FIG. 3. Twenty-one clones with different levels of large T antigen expression were expanded and tested for their ability to support DNA replication of the Py ori-containing plasmid, pNK-Ori-EGFP as shown in the Southern blot of FIG. 4. pNK-Ori-EGFP was transfected into CHO-T clones. Low molecular weight DNA was extracted by the method of Hirt extraction as described above. The state of methylation of pNK-Ori-EGFP was measured as an indirect assay of replication. Hirt-extracted DNA was purified and digested with DpnI and SpeI after which Southern blot hybridisation was performed. A probe consisting of $^{32}$P-labelled EGFP was used to detect plasmid DNA. Replication in mammalian cells results in plasmid DNA that is resistant to digestion with the endonuclease enzyme DpnI, while non-replicating plasmid DNA is sensitive to DpnI digestion and results in a number of small fragment due to the number of i sites in the plasmid. Results indicate that a number of CHO-T clones (FIG. 4; lanes 5 to 24) are capable of supporting replication of Py ori-containing DNA as evidenced by resistance to DpnI digestion.

Clone P1-C11 (FIG. 4, lane 11; CHO-T) was chosen for further studies as described in the following section.

(b) Development of NS0-T Cell Line

A stable NS0-T cell line was developed through the stable integration of pCMV-LT in order to provide a ready made level of large-T-antigen (LT) for future transient transfection of Py-ori containing plasmids. In this way plasmids may be replicated quickly to high copy number with no time wasted in waiting for LT to be expressed.

The stable integration was achieved using electroporation. Briefly, three cultures were electroporated containing: no DNA (negative control), pEGFP-C1 plasmid (positive control) or pCMV-LT plasmid (pLT). Cells were then grown in selection (G418) to determine if the neomycin resistance gene carried on pLT was stably integrated. The viability of the cultures was recorded over a period of three weeks to determine this. Samples of the negative and positive control were acquired using the fluorescent activated cell sorter (FACS) after 24 hours. This was to determine if any plasmid DNA had successfully entered cells following the electroporation procedure. The positive control exhibited EGFP fluorescence while the negative did not (data not shown).

The viability of the positive control, negative control and the pLT cultures all dropped immediately post transfection before they recovered after 2 days. The positive culture reached a viability of 93% after 4 days. The negative control and the pLT containing culture both followed a similar curve to each other for the first 7 days. The negative control however did not decrease as much as the pLT culture for the first two days. After the second day the viability of each decreased rapidly. The negative control reached 0% viability after 15 days while the pLT containing sample dropped to 2% viability after 9 days before recovering to 88% after 21 days post transfection (data not shown).

EXAMPLE 4

Growth Characteristics of CHO-T Cells

Growth in suspension: The CHO-T cell line (clone P1-C11) was adapted to growth in suspension in serum-free media (Excell302) and protein-free media Excell325.

CHO-T cells can be grown in suspension in a highly reproducible manner, which makes it very suitable for large-scale production. Biopharmaceutical production in mammalian cells has moved from attached culture to suspension culture. Suspension cultures are relatively simple to operate and easy to scale up. Suspension cells can attain higher biomass per volume of media for increased productivity. Furthermore, using suspension cells, homogenous conditions can be provided in a bioreactor which would allow precise monitoring and control of process parameters such as temperature, dissolved oxygen and pH. Hence this would allow more products to be produced and harvested with ease at a prolonged continuous pattern. This characteristic is superior to adherent cells for protein production.

Serum independence: CHO-T cells can be cultured and grown to high cell densities in protein-free synthetic media. Thus, safety is enhanced due to the absence of human or animal proteins in the culture.

Growth kinetic studies were carried out by growing the cells in 250 ml spinner flasks using 50 ml of media. Growth of CHO-T cells was compared to that of CHOXL99 (a CHO-K1 cell line also adapted to suspension growth). Cells were seeded at $3\times10^5$ cell/ml in Excell302 media and cell counts were taken daily for 8 days or until the viability dropped below 50%. Results are shown in FIG. 8. CHO-T cells have a peak viable cell density of $2.85 \times 10^6$ cell/ml with a doubling time of 21.23 hr compared to CHOXL99 having a peak viable cell density of $2.75 \times 10^6$ cells/ml with a doubling time of 20.01 hr.

EXAMPLE 5

Py Ori-containing Expression Vectors Replicate in CHO-T Cells

Plasmid replication within a mammalian cell requires the following three elements: 1) a viral origin of DNA replication 2) the associated viral transacting protein to initiate DNA replication and 3) permissive host-specific proteins. We have combined these elements in an expression system consisting of the Py ori-containing expression vector, the transacting viral protein, large T, expressed constitutively in the host cell line CHO-K1, which is permissive to Py replication. Plasmid pPyOri-EGFP was transfected into CHO-T and plasmid DNA replication was monitored over 3 days by determining the amount of plasmid DNA that has undergone one or more rounds of DNA replication using the methylation specific DpnI enzyme digestion method described above. As shown in FIG. 5, the total amount of non-replicating DNA drops consistently following transfection, while that of replicating DNA increases on day 2, but later drops (as shown in FIG. 5B).

These studies indicate that pPyOri-EGFP replicates several times in a CHO cells expressing Py Large T antigen giving rise to high copy number per cell as shown by an increase from 500 copies on day 1 to 3000 copies on day 2. FIG. 6 demonstrates that the increase in plasmid copy number is followed by an increase in EGFP expression. Similarly, a decrease in plasmid copy number on day 3 is followed by a decrease in gene expression (FIGS. 5 & 6). The drop in plasmid DNA, and hence recombinant gene expression, soon after transfection limits the use of Py ori-containing vectors to 3-4 days in a transient expression system. Accordingly, it is desirable to extend the window of transient gene expression. To this end, we developed episomal vectors that not only are capable of replicating in CHO cells but are also capable of stable plasmid maintenance as episomes which greatly extends the time period for transient expression of proteins in transfected cells. Epstein-Barr virus elements (EBNA-1 and OriP) were chosen to complement Py ori-based plasmid replication. EBV vectors anchor to the nuclear matrix through a high-affinity matrix attachment region containing the OriP sequence (Jankelevich et al. 1992; Mattia et a. 1999). Interaction of OriP with the origin binding protein, EBNA1 is required for EBV vector replication, maintenance and segregation (Lupton and Levine 1985; Polvino-Bodnar and Schaffer 1992; Yates et al. 1984) in primate cells. Episomal vectors based on EBV components have been used extensively for transgene expression (Sclimenti, C. R., 1998). EBV oriP and EBNA1 together confer stable episomal maintenance of viral DNA in the cell. These two sequences are necessary and sufficient for retention and replication of the EBV vector in a variety of established cells including human, monkey and dog (Sclimenti C. R., 1998). However, EBV vectors are not known to replicate in CHO cells due to the cells' non-permissive nature to EBV viral propagation.

Four plasmids were designed and constructed containing Py ori and/or EBV elements as depicted in FIG. 8. Plasmid pEBV contains the cis-acting sequence EBV origin of DNA replication (OriP) and encodes the Epstein-Barr Nuclear antigen-1 (EBNA1). Plasmid pPyOri contains Py ori without EBV sequences. Plasmid pEBV-PyOri contains OriP, EBNA1 of EBV and ori of Py. Plasmid pBasic lacks both EBV and Py viral elements. The reporter genes d2EGFP or hGH were cloned into all the above plasmids under the control of the constitutive CMV promoter. Detailed plasmid maps are shown in FIG. 1.

Retention and Segregation of pPyEBV vector

Figure 9A:
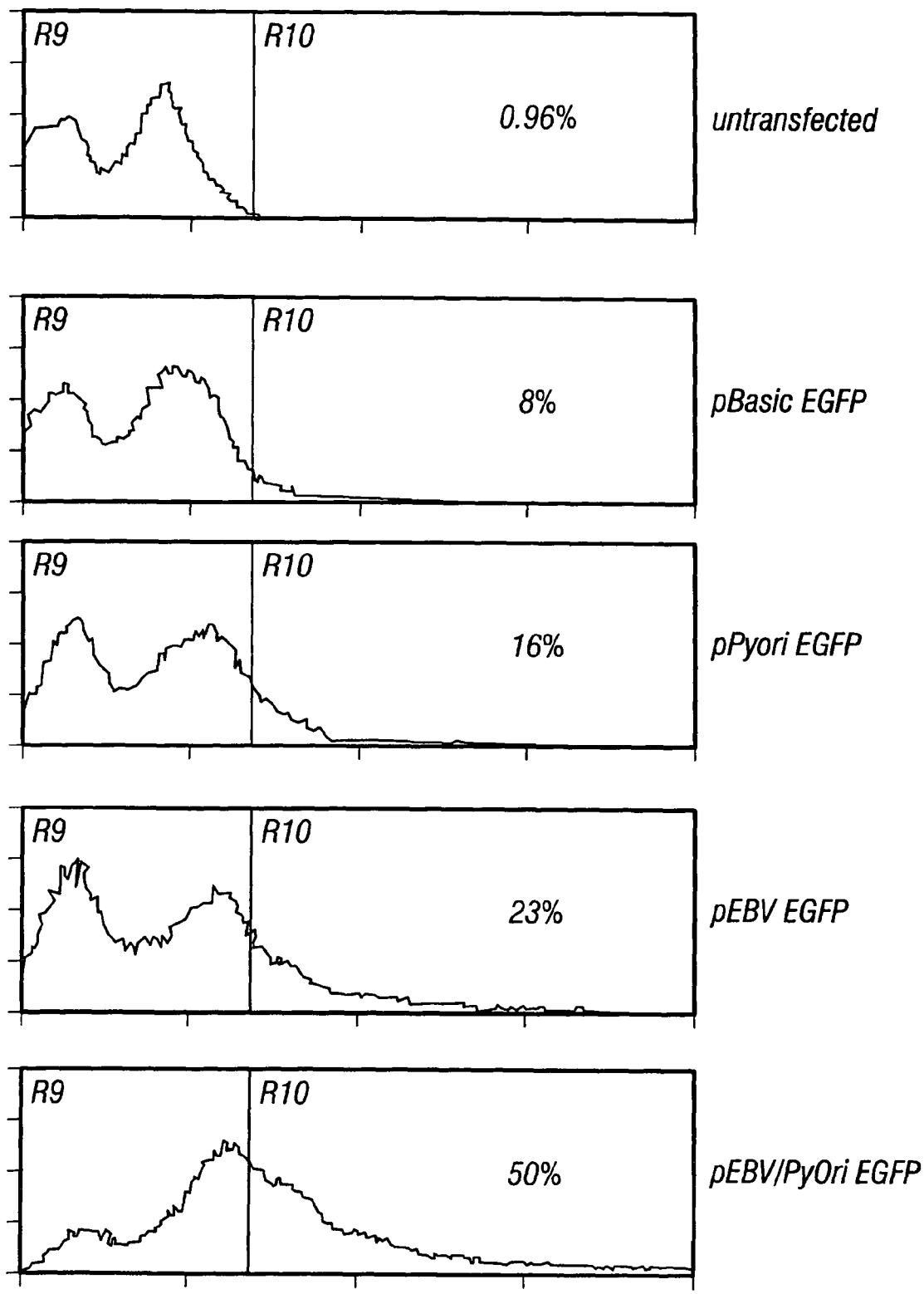
Figure 9B:
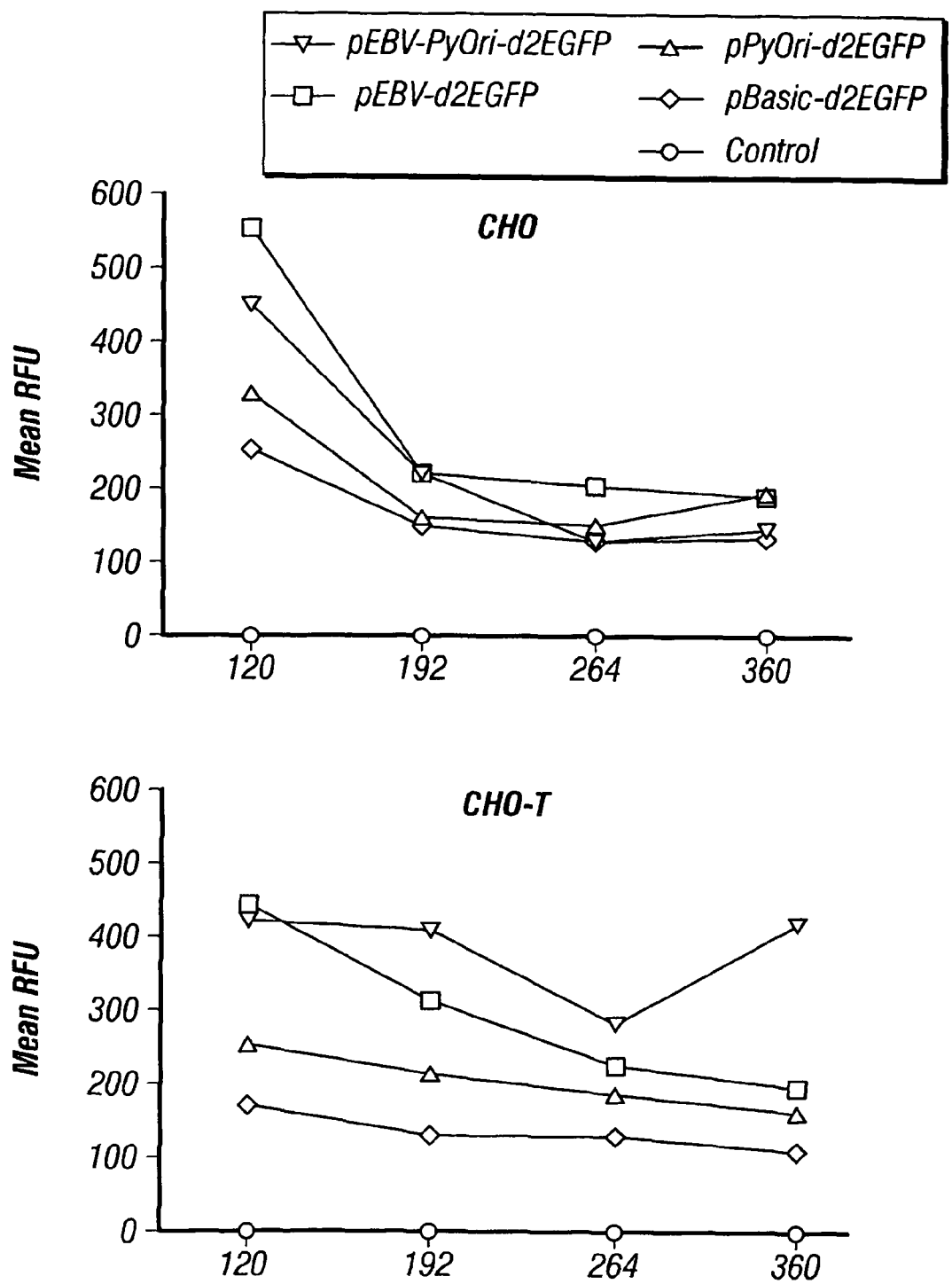
Figure 10A:
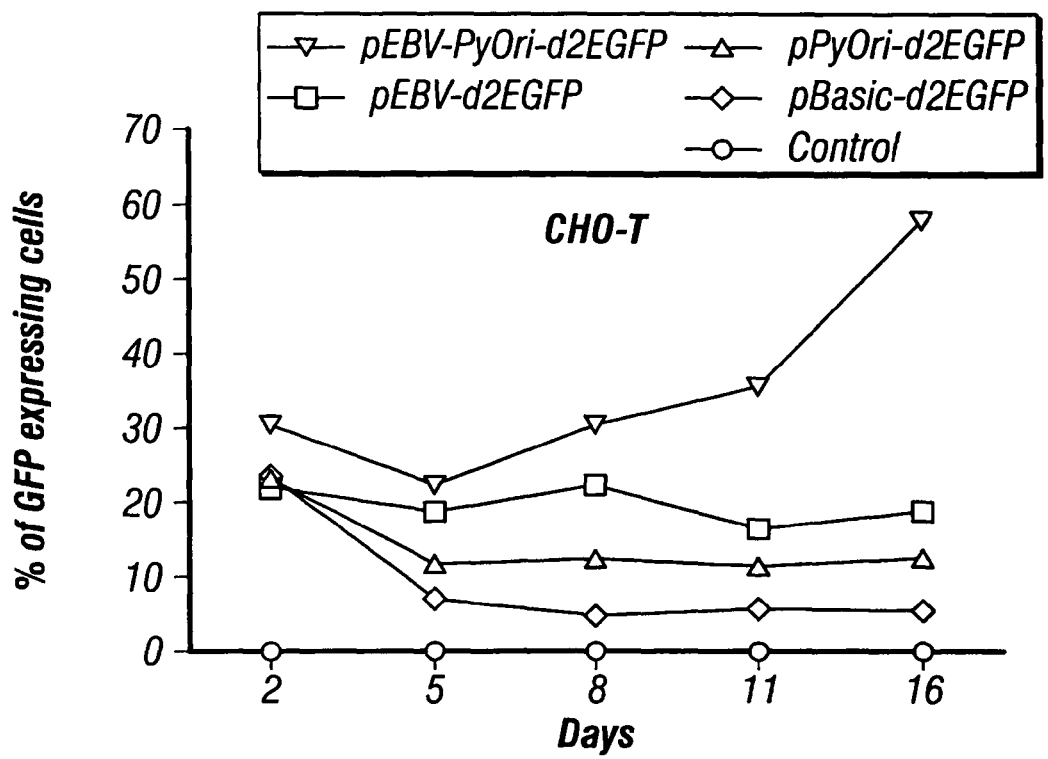
Figure 10B:
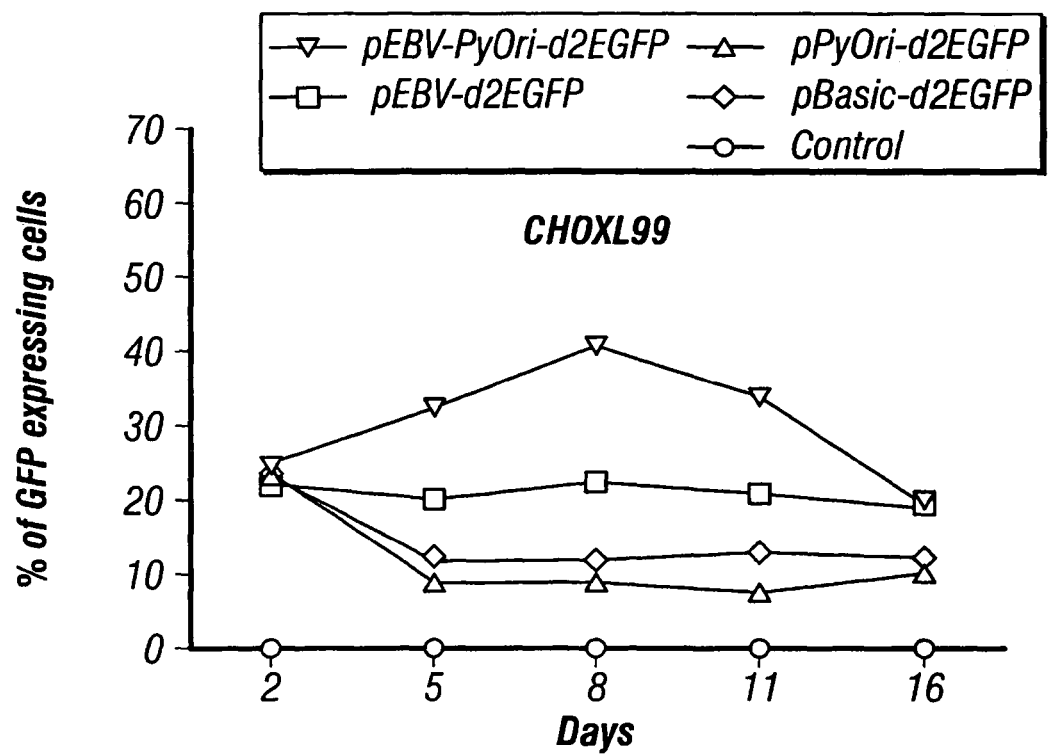
Figure 10C:
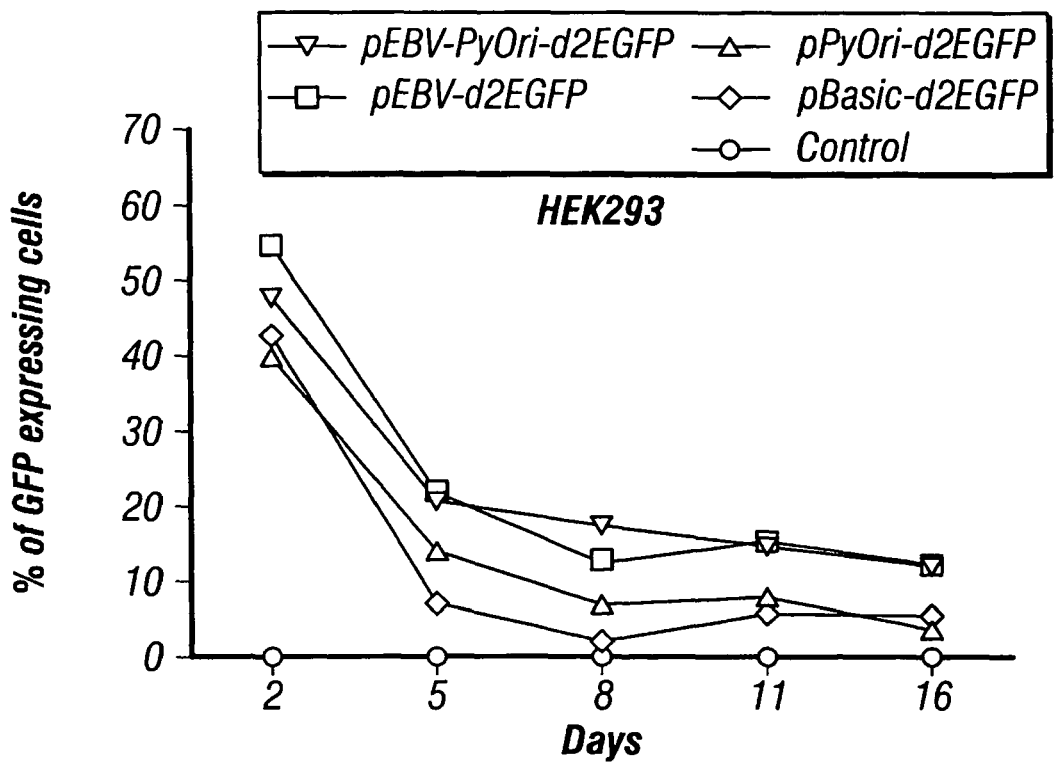
Figure 11A:
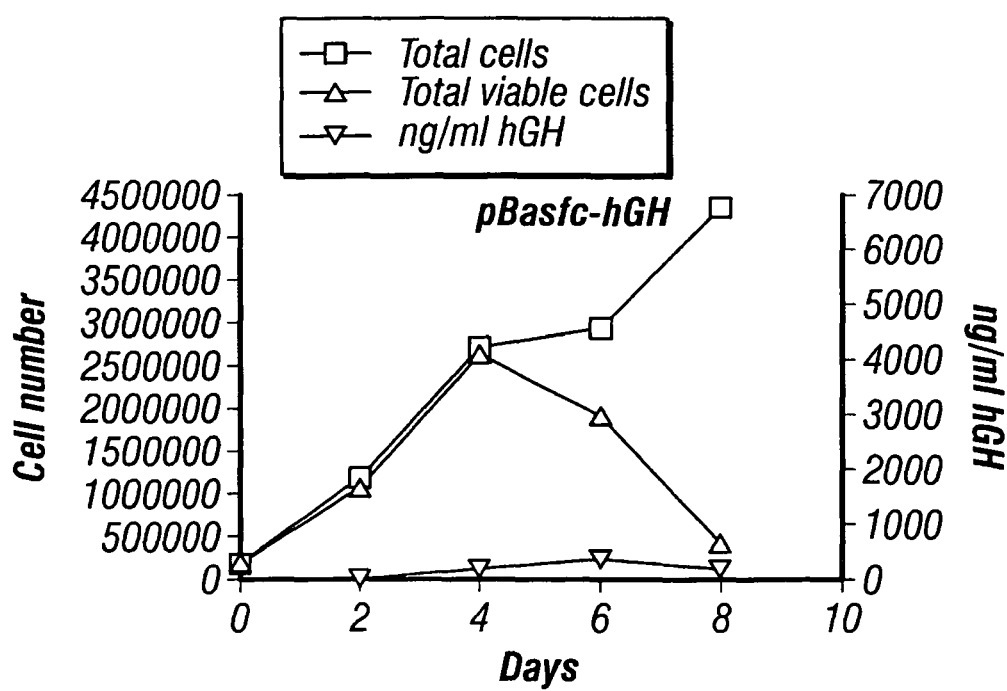
Figure 11A:
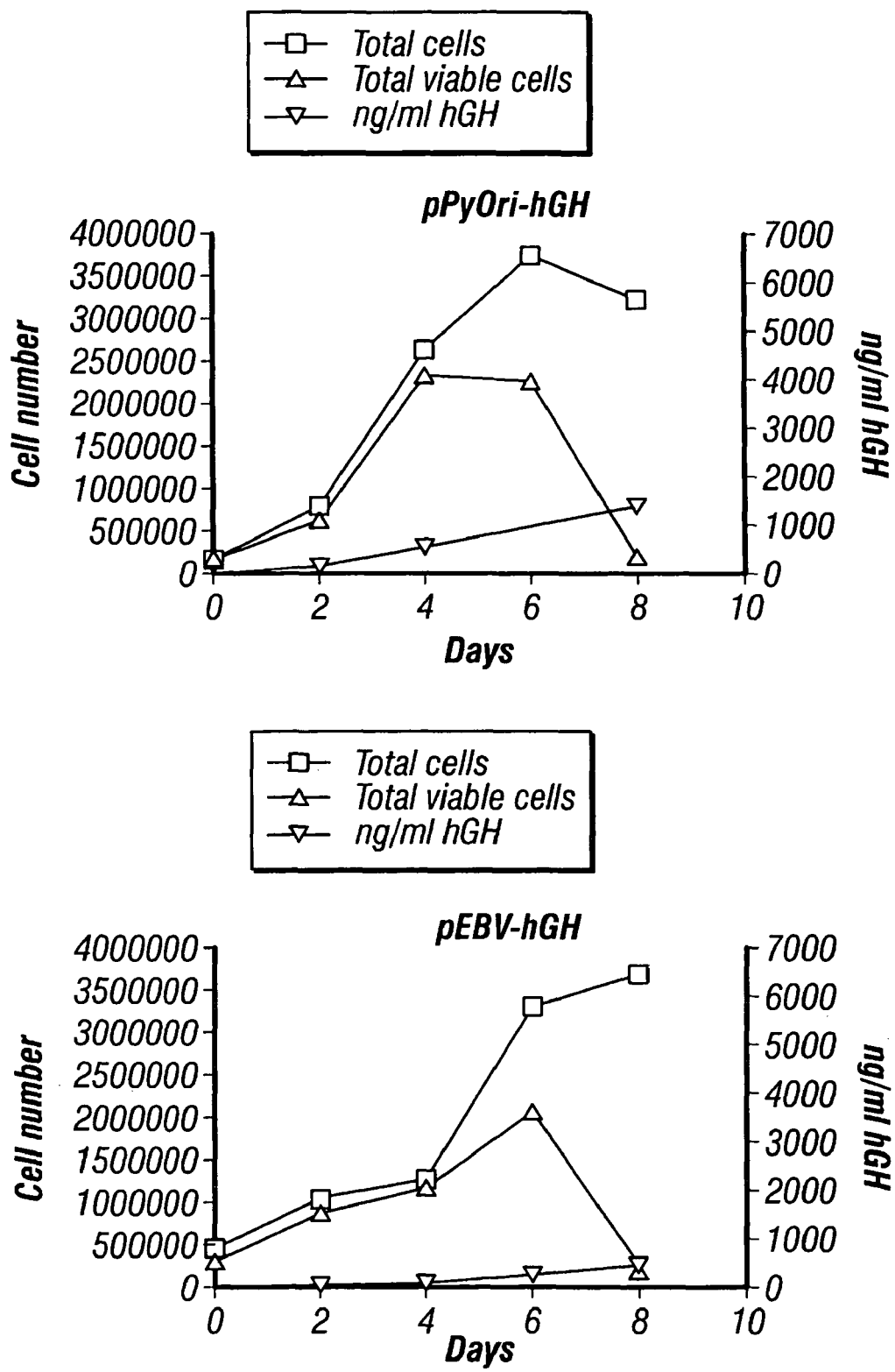
Figure 11A:
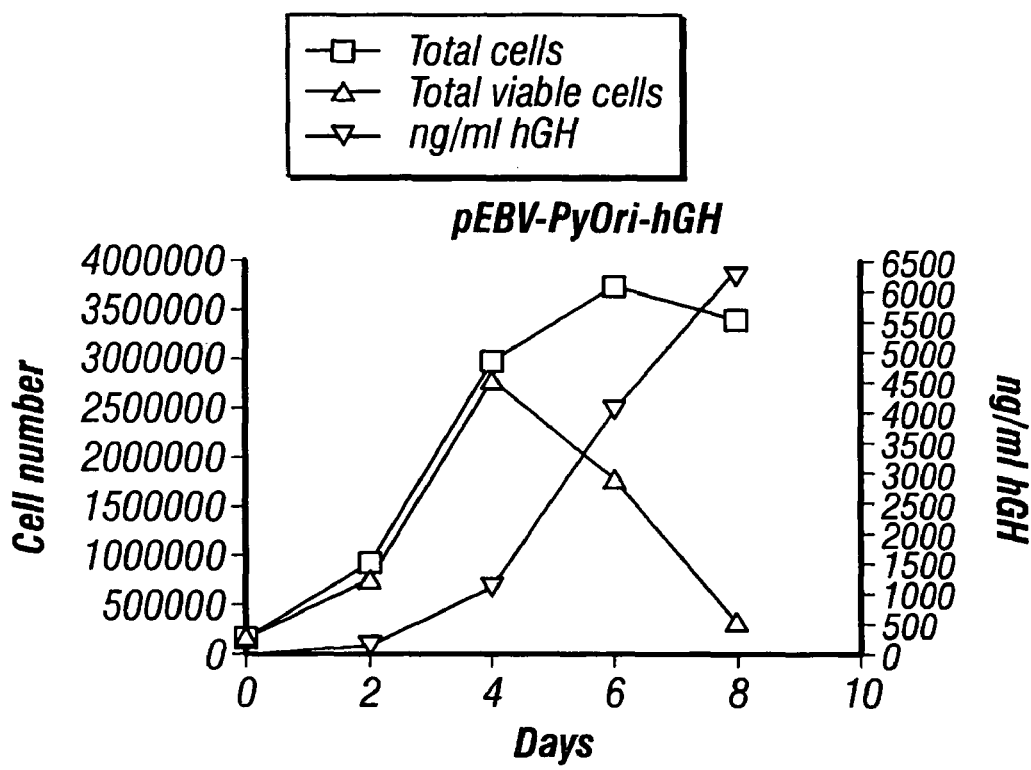
Figure 11B:
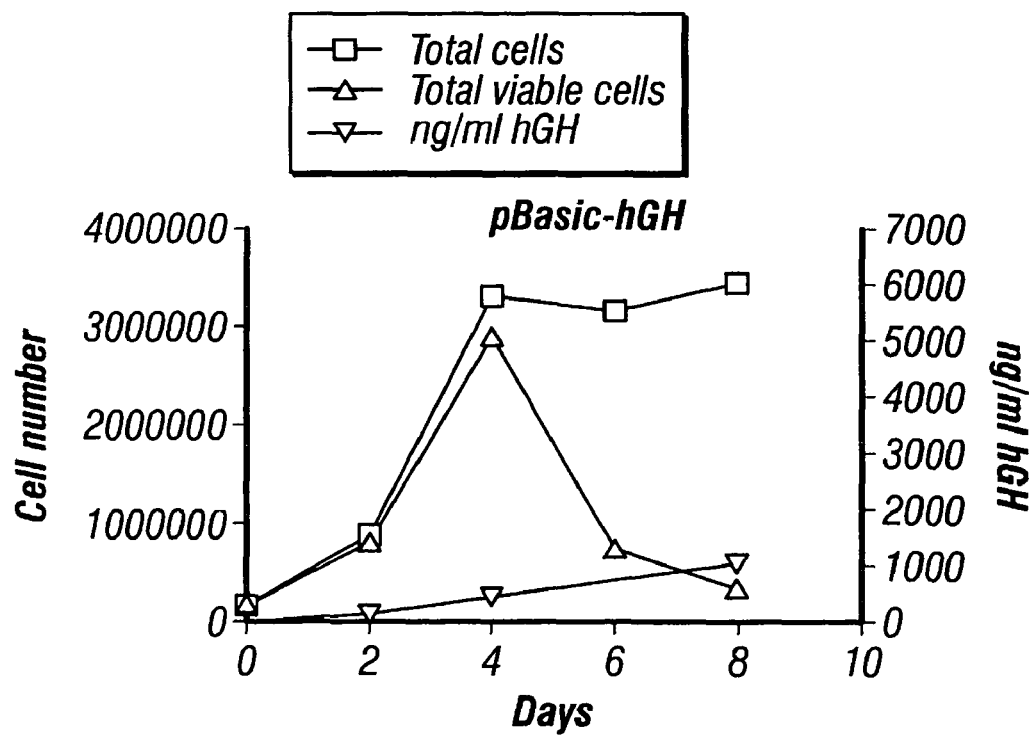
Figure 11B:
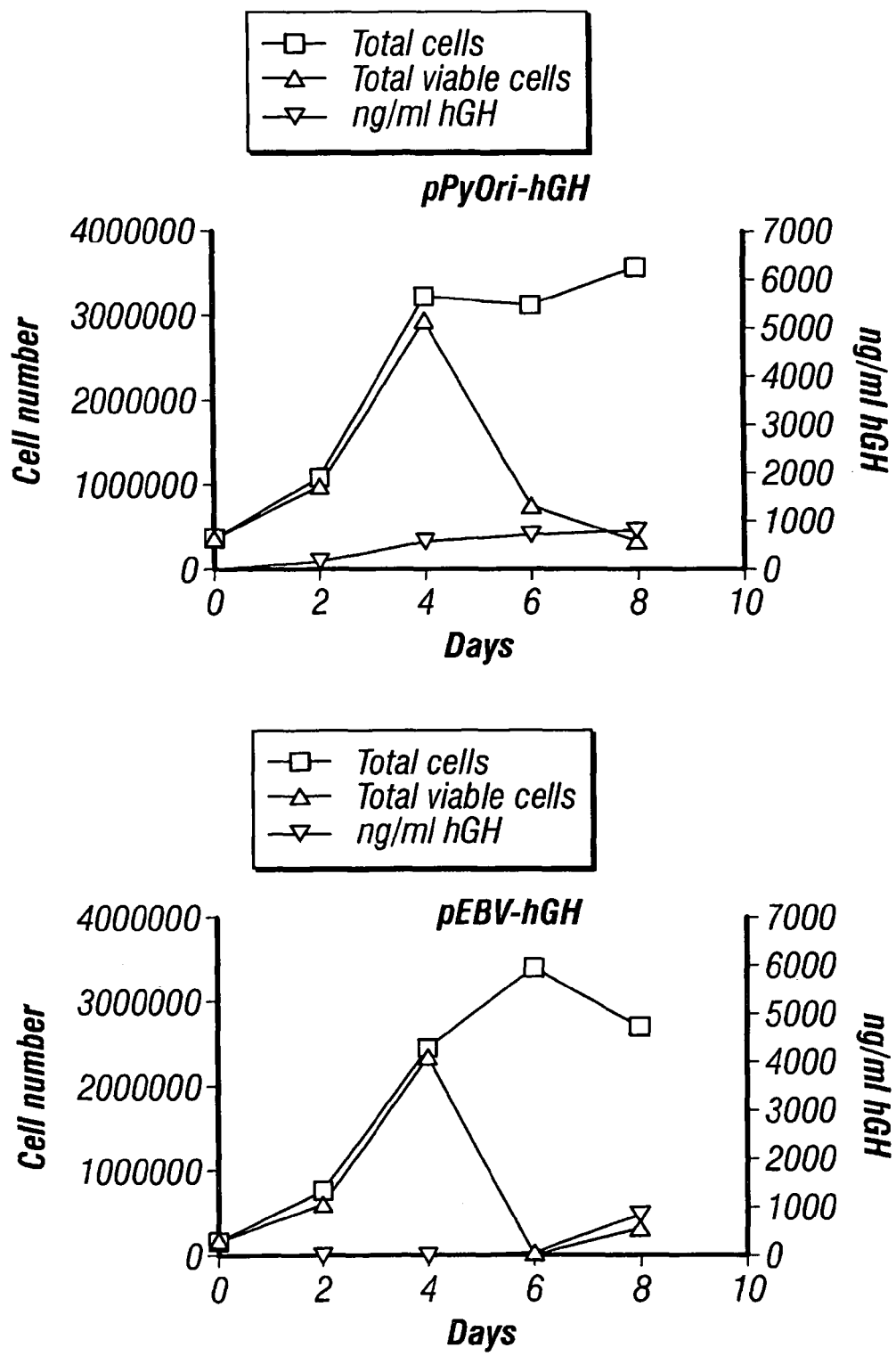
Figure 11B:
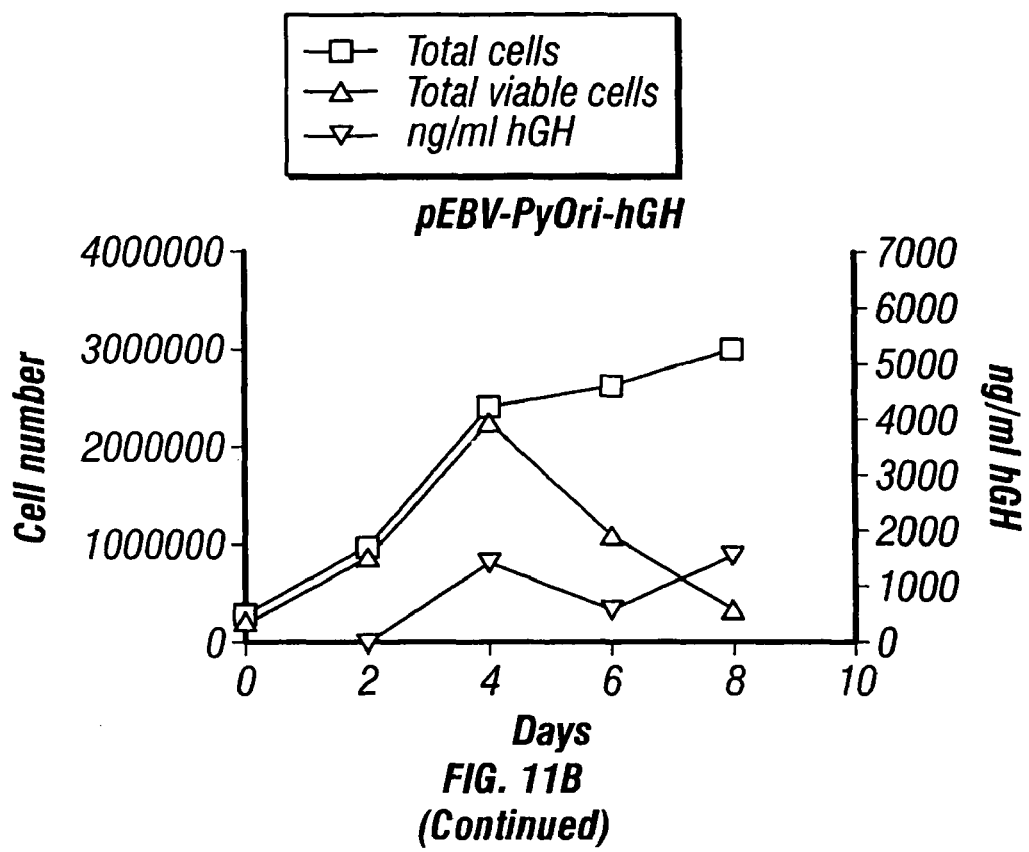

CHO-T, CHOXL99 and the human embryonic kidney (HEK) 293 cells were each transfected with individual plasmid constructs encoding the marker protein EGFP and selected in hygromycin-containing media at a concentration of 400 ug/ml. Cultures were analysed by flow cytometry following transfection to determine the percentage of GFP expressing cells (FIG. 9A) and the relative mean fluorescence (RFU) (FIG. 9B). CHO-T cells show an overall increase in the percentage of GFP expressing cells when transfected with pEBV-PyOri-d2EGFP (FIG. 10A). FIG. 10A shows that the pool of transfected CHO-T cells underwent an increase in the percentage of EGFP expressing cells when transfected with pEBV-PyOri-d2EGFP, the effect being most marked between days 11-15.). However CHO-T cells transfected with either with pEBV-d2EGFP, pPyOri-d2EGFP or pBasic-d2EGFP show no such increase in GFP expressing cells over time (FIG. 10A). In contrast, transfected CHOXL99 (FIG. 10B) and transfected HEK (FIG. 10C). do not show an increase in GFP-expressing cells (except for an initial increase pEBV-PyOri-d2EGFP in CHOXL99 cells). These results indicate that the number of CHO-T cells that harbour the pEBV-PyOri-d2EGFP begins to increase presumably due to plasmid replication (Large T antigen initiates replication from Py ori) and plasmid maintenance and segregation (interaction of EBNA-1 and OriP) (Lupton and Levine, 1985). This is not observed for other plasmid constructs. Although pPyOri-d2EGFP is capable of episomal replication in CHO-T cells the number of fluorescent cells decreases with time possibly due to the loss of plasmid DNA through degradation and cell division (FIGS. 10C and 10E). CHOXL99 cells which do not support PyOri-containing constructs (due to the absence of Large T antigen) demonstrate an increase in fluorescent cells when transfected with pEBV-PyOri-d2EGFP and selected in hygromycin for up to 8 days, but then declines (FIG. 10B). It is not understood at this time the reason for this observation. HEK 293 cells demonstrate high transfection efficiencies (FIG. 10C). However, the number of fluorescent cells declines rapidly for all constructs tested. This study has not confirmed replication of pEBV-d2EGFP and pEBV-PyOri-d2EGFP in HEK 293 cells although it would be expected that these plasmids would be capable of DNA replication in HEK 293 cells, due to the interaction of EBNA-1 and OriP and the presence of host-specific factors in the permissive HEK cell line.

EXAMPLE 6 hGH Production in Transient Transfection using CHO-T Cells and CHO XL99

Protein production was determined in CHO-T and CHOXL99 cells transfected with each of the four expression vectors encoding the human growth hormone gene (HGH). Cells were transfected as described above and seeded into 6-well microtitre plates at a density of $3 \times 10^5$ cells/ml. Cells were cultured for up to 8 days without addition of fresh media. Cell number, cell viability and HGH productivity were recorded daily. As shown in FIG. 11, transfected cells reached a peak cell density of approximately $3.5-4 \times 10^6$ cells/ml for each set of transfections. Cells transfected with vectors that are unable to replicate in CHO-T cells (pBasic-hGH, pEBVhGH, and all vectors in CHOXL99 cells) had protein yields of approximately 1 ug/ml hGH or less, while yield in CHO-T cells transfected with pPyOri-hGH was slightly higher. In contrast, CHO-T cells harbouring the expression vector pEBV-PyOri-hGH had protein yield in excess of 6 ug/ml. These results indicate that the high level of transient protein yield is likely to be due to the increase in copy number as a result of plasmid replication and segregation. Although the plasmid pPyOri-hGH is capable of replication in CHO-T cells, these cultures resulted in a final product yield of only 2 mg/L. These data indicate that the difference in product concentration is due to more than simply plasmid replication alone. Total and viable cell densities of both transfected CHO-T and CHO cells were similar indicating that episomal replication does not adversely affect growth of these cells.

Scaled Transient Production of hGH

Large-scale transfection of mammalian cells has emerged for the fast production of milligram amounts of recombinant proteins (Jordan et al 1998; Schlaegar et al 1999; Wurm and Bernard, 1999; Durocher et al 2002). The present expression system (CHO-T cell line and DNA expression vector pEBV-PyOri) was tested for scaled-up protein production of hGH. Cells were transfected with either the replication-competent expression vector pPyEBV-hGH or the replication incompetent vetor, pBasic-hGH. Cells were seeded at a concentration of $5 \times 10^5$ cells/ml and cultured in spinner culture flasks in a total volume of 100 ml. As shown in FIG. 12, both cultures reached similar maximum viable cell numbers with viability remaining above 90% of total cell numbers up to 4 days post inoculation followed by a rapid decline in viability presumably due to nutrient depletion. Product yields were 10 mg/L and 30 mg/L in pBasic-hGH (A) and pPy EBV-hGH (B) transfectants respectively. The increased yield in productivity in CHO-T cells transfected with pEBV-OriPy-hGH results from plasmid replication and segreation. In a subsequent semi-continuous batch culture, a media replacement strategy (50% every 48 h) was used to extend the viability of the cultures. FIG. 13 shows the growth profile and productivity obtained from a transient transfection in CHO-T cells transfected with pEBV-OriPy-hGH as a result of a media replacement feeding strategy following inoculation. Although the maximum viable cell densities reached were similar to those obtained in the previous batch study, the feeding strategy allowed for improved cell viability for longer periods without undergoing a sharp decline. Using this strategy, cell viability was maintained and cumulative protein yield reached a concentration of 75 mg/L with a calculated maximum specific productivity of 7.8 pg/cell/day. Such a feeding strategy presumably allows for continued cell dvision and hence plasmid replication. Accordingly, plasid replication, retention and segregation taken together resulting in an increase in recombinant gene expression capabilities and enhanced product yield.

EXAMPLE 7

Large T Antigen can Inhibit the Onset of Apoptosis

A comparison of viabilities of CHO-T and CHOXL99 cells as illustrated in FIG. 7 shows that CHO-T cells have cell viabilities that exceed that of the parental cell line, XL99. CHO cells expressing large T antigen may also exhibit the beneficial effect of being resistant to apoptosis. Eukaryotic cell culture has become a billion-dollar industry, generating products of commercial importance over a span of decades. However, eukaryotes are considerably more fragile than bacteria and environments typically associated with large-scale culture often lead to significant levels of cell death due to programmed cell death or apoptosis.

One of the most common causes of apoptosis in typical bioreactor configurations is the deprivation of nutrients or specific survival factors from the cell-culture medium. Many studies have been undertaken to identify nutritional strategies that can enhance the viability and productivity of cell lines used in commercially relevant biotechnological processes. By prolonging cell survival the yield of valuable proteins such as monoclonal antibodies can be improved, as protein production is primarily a function of the viable cell population.

The mechanism of apoptosis intervention is similar to that described for E1B 19 kDa protein. It has been shown that polyomavirus LT can overcome p53-induced growth arrest which leads to programmed cell death or apoptosis (Rodier et al., (2000)). It accomplishes this by its association with and inactivation of the Rb proteins.

EXAMPLE 8

Sodium Butyrate Comparison

Gene expression is enhanced in CHO cells expressing large T antigen. Not to be bound by theory, it is thought that as CHO cells expressing large T mimic the gene activating effects of sodium butyrate, that a similar mechanism may be responsible. Sodium butyrate is a histone deacetylase (HDAC) inhibitor, which increases gene expression presumably by inactivating the cell retinoblastoma protein Rb (Buquet-Fagot et al., (1996), Luo et al., (1998), and Struhl, (1998)). Sodium butyrate has often been used in production processes to increase recombinant gene expression and protein productivity. However, the addition of sodium butyrate also results in cellular growth arrest and the onset of apoptosis; and therefore, is only added in the final stages of a production process. The constitutive expression of large T antigen in CHO-T cells mimics the effects of sodium butyrate for increasing gene expression without causing growth arrest; and therefore can be used throughout the production process to yield consistently high specific productivity (FIG. 14).

Enhanced Transfection Efficiencies in CHO-T Cells

CHO-T cells (CHO-K1 cells stably expressing polyoma virus large T antigen, PyLT) provide a mechanism of enhanced transgene expression when transfected with plasmids carrying polyoma virus ori sequences.

Not wishing to be bound by theory, it is assumed that the transfection efficiency of CHO-T is enhanced in comparison to CHO due to the presence of nuclear localization signals (NLSs) on PyLT. NLS are known to be involved in the active transport of exogenous proteins into the nucleus via their interaction with the nuclear import machinery (Nagasaki et al., (2003), Dean., (1997)). It has been shown that plasmid DNA—NLS peptide conjugates can increase the expression efficiency of plasmid DNA. Plasmid DNA containing Polyoma virus ori sequences contain a number of PyLT binding sites to which PyLT binds.

Discussion

This work describes a mammalian expression system that is not only capable of episomal replication but of retention of the episome in CHO cells. The expression system consists of the vector pEBV-OriPy and CHO-T cells and is designed for use in large-scale transient production of recombinant protein for early product development purposes. To date, the most successful examples of the use of transient expression systems to manufacture recombinant proteins at scale have employed suspension adapted transformed human embryonic kidney HEK293(EBNA) host cells, engineered to express EBNA-1. In combination with plasmid vectors harbouring the OriP origin of replication, this system enables both nuclear retention and autonomous replication of episomal plasmid DNA (Langle-Rouault et al. 1998; Sclimenti and Calos 1998; Van Craenenbroeck et al. 2000). HEK293 (EBNA) cells have been employed in batch production processes for a variety of recombinant proteins derived from transiently transfected pools, yielding up to 20 mg $L^{-1}$ (Durocher et al. 2002; Girard et al. 2002; Meissner et al. 2001).

A transient expression system at least as efficient as the HEK293(EBNA) system has not been utilised for scaled-up transient production in CHO cells. It is well known that different host cell types confer different post-translational modifications, which may significantly affect the properties of therapeutic recombinant proteins. The same recombinant protein produced by both HEK293 and CHO cells may have a different bioactivity in vitro (Haack et al. 1999). HEK293 cells for example, are known to differ from CHO cells with respect to N-glycan processing (Van Craenenbroeck et al. 2000; Yates et al. 1984). The ability to transiently produce recombinant proteins at an early stage in product screening/development in the same host cell type that would likely be employed for the final bioprocess is clearly advantageous. Epstein-Barr-based vectors are incapable of replicating in CHO cells on their own. In this study we have shown that transient gene expression is greatly enhanced if replication occurs via the interaction of PyOri and PyLT. The rodent Polyomavirus origin of DNA replication interacting with PyLT results in extrachromosomal plasmid replication in CHO cells. Nuclear retention and segregation of transfected DNA to daughter cells is ensured by the interaction of EBNA-1 and OriP. The combination of both Polyomavirus and EBV sequences results in increased gene copy number within the transfected cells and sustained gene expression and protein production in CHO cells. We have shown that the expression system described herein can produce up to 75, g/L of recombinant protein with in 10 days of transfection.

Conclusions

Extrachromosomal vectors that replicate stably and are retained in cells over the long term are useful tools for studying gene expression, DNA replication, repair, recombination, and other cellular processes, and have potential importance for gene therapy. Such vectors have been previously unavailable for rodent cells even though these cells are commonly used in understanding the biology of mammalian systems.

There are several advantages of episomal vectors; first, the inserted gene of interest cannot be interrupted or subjected to regulatory constraints, which often occur from integration into cellular DNA. Secondly, the presence of the inserted heterologous gene does not lead to rearrangement or interruption of the cell's own important regions. Thirdly, episomal vectors persist in multiple copies in the nucleus, resulting in amplification of the gene of interest whenever the necessary viral trans-acting factors are supplied. Finally, the use of episomal vectors often results in a higher transfection efficiency than the use of chromosome-integrating plasmids.

Long-term replication and enhanced transgene expression induced by pEBVPyOri-based vectors in mammalian cells is a useful tool for the rapid production of sufficient amounts of recombinant protein for structural and functional analyses and high-throughput screening. In combination with gene transfer mechanisms such as cationic lipids this expression system provides an experimental model for gene therapy and for gene transfer experiments.

Although the invention has been described with reference to specific examples, it will be appreciated by those skilled in the art that the invention may be embodied in many other forms, in keeping with the broad principles and the spirit of the invention described herein.

REFERENCES

Bailey, C. G., Baig, M., Gray, P. P. and Sunstrom, N. A. (1999) A rapid selection/amplification procedure for high-level expression of recombinant protein in a metal-amplifiable mammalian expression system. *SO-Biotechnology Techniques.* 13(9). 615-619.

Bailey, C. G., Tait, A. S. and Sunstrom, N. A. (2002) High-throughput clonal selection of recombinant CHO cells using a dominant selectable and amplifiable metallothionein-GFP fusion protein. *Biotechnology & Bioengineering.* 80, 670-6.

Baker, K. N., Rendall, M. H., Hills, A. E., Hoare, M., Freedman, R. B. and James, D. C. (2001) Metabolic control of recombinant protein N-glycan processing in NS0 and CHO cells. *Biotechnology & Bioengineering.* 73, 188-202.

Buquet-Fagot, C., Lallemand, F., Charollais, R. H. and Mester, J. (1996) Sodium butyrate inhibits the phosphorylation of the retinoblastoma gene product in mouse fibroblasts by a transcription-dependent mechanism. *Journal of Cellular Physiology.* 166, 631-6.

Chu, G Hayakawa, H and Berg, P 1987. Electroporation for the efficient transfection of mammalian cells with DNA. Nucl. Acids Tes 15:1311-1326.

Cole, C. N. (1996) *Polyomavirinae: The viruses and their replication.* Lippincott-Raven:Philadelphia.

Dean, D. A. (1997) Import of plasmid DNA into the nucleus is sequence specific. *Experimental Cell Research.* 230, 293-302.

Durocher, Y., Perret, S., Kamen, A. (2002). High-level and high-throughput recombinant protein production by transient transfection of suspension-growing human 293-EBNA-1 cells. *Nucleic Aids Research.* 30(2):E9.;1

Gahn, T. A. and Schildkraut, C. L. (1989) The Epstein-Barr virus origin of plasmid replication, oriP, contains both the initiation and termination sites of DNA replication. *Cell* 58, 527-35.

Gassmann, M., Donoho, G. and Berg, P. (1995) Maintenance of an extrachromosomal plasmid vector in mouse embryonic stem cells. *Proceedings of the National Academy of Sciences of the United States of America.* 92, 1292-6.

Girard, P. M. D., Baumgartner, G., Bourgeois, M., Jordan, M., Jacko, B., and Wurm, F. M. (2002) 100 Liter-transient transfection. *Cytotechnology* 38: 15-22.

Gluzman, Y. (1981) SV40-transformed simian cells support the replication of early SV40 mutants. *Cell.* 23, 175-82.

Griffin, B. E. (1982) *Structure and genomic organization of SV40 and polyoma virus.* Cold spring harbor laboratory: New york.

Haack, A., Schmitt, C., Poller, W., Oldenburg, J., Hanfland, Pl, Brackmann, H. H., and Schwaab, R. (1999) Analysis of expression kinetics and activity of a new B-domain truncated and full-length FVIII protein in three different cell lines. *Annals of Hematology* 78(3):111-116.

Heffernan, M. and Dennis, J. W. (1991) Polyoma and hamster papovavirus large T antigen-mediated replication of expression shuttle vectors in Chinese hamster ovary cells. *Nucleic Acids Research.* 19, 85-92.

Hirt, B. (1967) Selective extraction of polyoma DNA from infected mouse cell cultures. *Journal of Molecular Biology.* 26, 365-9.

Jankelevich, S., Kolman, J. L., Bodnar, J. W. and Miller, G., (1992) A nuclear matrix attachment region organizes the Epstein-Barr viral plasmid in Raji cells into a single DNA domain. *EMBO Journal.* 11(3): 1165-76

Kieff, E. (1996) *Epstein-Barr Virus and its Replication*. Lippincott-Raven:Philadelphia.

Kitchen, N. (1998) Adaptation of CHO-K1 to suspension growth.

Krysan, P. J. and Calos, M. P. (1993) Epstein-Barr virus-based vectors that replicate in rodent cells. *Gene*. 136, 137-43.

Langle-Rouault, F., Patzel, V. Benavente, A., Taillez, M., Silvestre, N., Bompard, A., Sczakiel, G., Jacobs, E. and Rittner, K. (1998) Up to 100-fold increase of apparent gene expression in the presence of Epstein-Barr virus oriP sequences and EBNA1: Implications of the nuclear import of plasmids. *Journal of Virology* 72(7): 6181-6185

Lindahl, T., Adams, A., Bjursell, G., Bornhamm, G. W., Kaschka-Dierich, C. and Jehn, U. (1976) Covalently closed circular duplex DNA of Epstein-Barr virus in a human lymphoid cell line. *Journal of Molecular Biology*. 102, 511-30.

Luo, R. X., Postigo, A. A. and Dean, D. C. (1998) Rb interacts with histone deacetylase to repress transcription. *Cell*. 92, 463-73.

Lupton, S. and Levine, A. J. (1985) Mapping genetic elements of Epstein-Barr virus that facilitate extrachromosomal persistence of Epstein-Barr virus-derived plasmids in human cells. *Molecular & Cellular Biology*. 5, 2533-42.

Mattia, E., Ceridono, M., Chichiarelli, S, and D'Erme, M. (1999) Interaction of Epstein-Barr virus origins of replication with nuclear matrix in the latent and in the lytic phases of viral infection. *Virology*. 262(1): 9-17

Meissner, P., Pick, H., Kulangara, A., Chatellard, P., Friedrich, K., and Wurm, F. M. (2001). Transient gene expression: recombinant protein production with suspension-adapted HEK293-EBNA cells. *Biotechnology & Bioengineering*. 75(2): 197-203

Mizuguchi, H., Hosono, T. and Hayakawa, T. (2000) Long-term replication of Epstein-Barr virus-derived episomal vectors in the rodent cells. *FEBS Letters*. 472, 173-8.

Muller, W. J, Naujokas, M. A. and Hassell, J. A. (1984) Isolation of large T antigen-producing mouse cell lines capable of supporting replication of Py-plasmid recombinants. *Molecular & Cellular Biology*. 4, 2406-12.

Niller, H. H., Glaser, G., Knuchel, R. and Wolf, H. (1995) Nucleoprotein complexes and DNA 5'-ends at oriP of Epsteinn-Barr virus. *Journal of Biological Chemistry*. 270, 12864-8.

Page, M. J. and Sydenham, M. A. (1991) High level expression of the humanized monoclonal antibody Campath-1H in Chinese hamster ovary cells. *Bio/Technology*. 9, 64-8.

Piechaczek, C., Fetzer, C., Baiker, A., Bode, J. and Lipps, H. J. (1999) A vector based on the SV40 origin of replication and chromosomal S/MARs replicates episomally in CHO cells. *Nucleic Acids Research*. 27, 426-8.

Polvino-Bodnar, M., Schaffer, P. A. (1992) DNA binding activity is required for EBNA 1-dependent transcriptional activation and DNA replication. *Virology*. 187(2): 591-603

Reisman, D., Yates, J. and Sugden, B. (1985) A putative origin of replication of plasmids derived from Epstein-Barr virus is composed of two cis-acting components. *Molecular & Cellular Biology*. 5, 1822-32.

Rodier, F., Bertrand, R., Bossolasco, M. and Mes-Masson, A. M. (2000) Polyomavirus large T-antigen protects mouse cells from Fas-, TNF-alpha- and taxol-induced apoptosis. *Oncogene*. 19, 6261-70.

Sambrook, J., MacCallum, P. and Russell, D. (2001) *Molecular Cloning: a laboratory manual*. Cold Spring Harbor Laboratory Press: N.Y.

Sclimenti, C. R. and Calos, M. P. (1998) Epstein-Barr virus vectors for gene expression and transfer. *Current Opinion in Biotechnology*. 9, 476-9.

Struhl, K. (1998) Histone acetylation and transcriptional regulatory mechanisms. *Genes & Development*. 12, 599-606.

Van Craenenbroeck, K., Vanhoenacker, P., and Haegeman, G. (2000). Episomal vectors for gene expression in mammalian cells. *European Journal of Biochemistry*. 267(18):5665-78.

Yates, J., Warren, N., Reisman, D. and Sugden, B. (1984) A cis-acting element from the Epstein-Barr viral genome that permits stabel replication of recombinant plasmids in latently infected cells. *Proceedings of the National Academy of sciences of the United States of America*. 81, 3806-10.

Yates, J. L. and Guan, N. (1991) Epstein-Barr virus-derived plasmids replicate only once per cell cycle and are not amplified after entry into cells. *Journal of Virology*. 65, 483-8.

---

The claims defining the invention are as follows:

1. An expression system comprising a CHO cell, wherein the CHO cell comprises
   (a) a vector comprising a gene encoding a protein of interest,
   (b) (i) a gene capable of expressing a polyoma large T antigen and (ii) a polyomavirus origin of replication to initiate DNA replication of the vector; and
   (c) the oriP of Epstein Barr Virus (EBV) and the EBNA-1 gene of EBV.

2. The expression system of claim 1, wherein the CHO cell is provided with one or more functional benefits selected from
   (i) an increase in transfection efficiency,
   (ii) enhanced gene expression,
   (iii) the ability of the CHO cell to grow as a single cell suspension culture in protein free medium, and
   (iv) resistance of the CHO cell towards the onset of apoptosis.

3. The expression system of claim 1 or claim 2, wherein large T antigen is constitutively expressed by the rodent CHO cell.

4. The expression system of claim 1 or claim 2, wherein the large T antigen is transiently expressed by the CHO cell.

5. The expression system according to any one of claims 1 to 2, wherein the expression system is a stable episomal replicating system.

6. The expression system according to claim 5, wherein the replication and retention of the episomal replicating system lasts for greater than three weeks.

7. An expression vector for use in a CHO expression system, the expression vector comprising
   (a) (i) a gene capable of expressing a polyoma large T antigen and (ii) a polyomavirus origin of replication to initiate DNA replication of the vector; and
   (b) the oriP of Epstein Barr Virus (EBV) and the EBNA-1 gene of EBV.

8. The expression vector according to claim 7, wherein the vector is capable of episomal replication and long term stable episomal maintenance in the CHO cell.

9. A method for producing a protein of interest comprising culturing a CHO cell, the CHO cell comprising
   (a) a gene encoding the protein of interest on a vector,
   (b) (i) a gene capable of expressing a polyoma large T antigen and (ii) a polyomavirus origin of replication to initiate DNA replication of the vector; and
   (c) the oriP of Epstein Barr Virus (EBV) and the EBNA-1 gene of EBV, under conditions promoting expression of said protein, and recovering said protein.

10. The method of claim 9, wherein the gene capable of expressing a polyoma large T antigen is constitutively expressed by the CHO cell.

11. The method of claim 9, wherein the gene capable of expressing a polyoma large T antigen is transiently expressed in the CHO cell.

12. The method of any one of claims 9 to 11, wherein the EBNA-1 gene of EBV is constitutively expressed by the CHO cell.

13. The method of any one of claims 9 to 11, wherein the EBNA-1 gene of EBV is transiently expressed by the CHO cell.

14. A method for producing a recombinant protein, comprising the step of culturing a CHO-1 cell comprising the expression vector according to any one of claims 7 to 8 under conditions promoting expression of said protein, and recovering said protein.

15. A CHO cell transformed with a vector according to any one of claims 7 to 8.

16. A method of increasing resistance to apoptosis in a CHO cell comprising expressing (i) polyoma large T antigen (ii) a polyomavirus origin of replication to initiate DNA replication of the vector; and (iii) the oriP of Epstein Barr Virus (EBV) and the EBNA-1 gene of EBV in the cell.

17. The method of claim 16, wherein the polyoma large T antigen is expressed constitutively by the CHO cell.

18. The method of claim 16, wherein the polyoma large T antigen is expressed transiently by the CHO cell.

* * * * *

SEQUENCE LISTING

```
<160> NUMBER OF SEQ ID NOS: 2

<210> SEQ ID NO 1
<211> LENGTH: 36
<212> TYPE: DNA
<213> ORGANISM: artificial
<220> FEATURE:
<223> OTHER INFORMATION: vector primer PyOri-ClaI-S

<400> SEQUENCE: 1
actacatcga tcagtctccc tcgatgaggt ctacta                      36

<210> SEQ ID NO 2
<211> LENGTH: 36
<212> TYPE: DNA
<213> ORGANISM: Artificial
<220> FEATURE:
<223> OTHER INFORMATION: Vector Primer PyOri-ClaI-AS

<400> SEQUENCE: 2
tactcatcga tctacgtatc catgatggtg gtgagg                      36
```